United States Patent
Liu et al.

(10) Patent No.: US 12,297,485 B2
(45) Date of Patent: May 13, 2025

(54) ELECTROCHEMICAL BIOSENSOR AND USES THEREOF

(71) Applicant: UNIVERSITY OF CONNECTICUT

(72) Inventors: Changchun Liu, Farmington, CT (US); Ziyue Li, Storrs, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 434 days.

(21) Appl. No.: 17/812,876

(22) Filed: Jul. 15, 2022

(65) Prior Publication Data

US 2023/0041450 A1    Feb. 9, 2023

Related U.S. Application Data

(60) Provisional application No. 63/222,989, filed on Jul. 17, 2021.

(51) Int. Cl.
| | | |
|---|---|---|
| *C12Q 1/6825* | (2018.01) | |
| *C12Q 1/6823* | (2018.01) | |
| *G01N 27/327* | (2006.01) | |

(52) U.S. Cl.
CPC ......... *C12Q 1/6825* (2013.01); *C12Q 1/6823* (2013.01); *G01N 27/3276* (2013.01)

(58) Field of Classification Search
None
See application file for complete search history.

(56) References Cited

PUBLICATIONS

Broughton, J.P., et al., CRISPR-Cas12-based detection of SARS-CoV-2, Nat. Biotechnol. 38, 870-874, Jul. 2020.

Brown, M.R., et al., AC electroosmotic flow in a DNA concentrator, Microfluid Nanofluid (2006) 2: 513-523, May 20, 2006.

Bruch, R., et al., CRISPR/Cas13a-Powered Electrochemical Microfluidic Biosensor for Nucleic Acid Amplification-Free miRNA Diagnostics, Adv. Mater. 31, 1905311, Oct. 30, 2019.

Chen, J.S., et al., CRISPR-Cas12a target binding unleashes indiscriminate single-stranded DNase activity, Science 360, 436-439 (2018) Apr. 27, 2018.

Dai, Y., et al., Exploring the Trans-Cleavage Activity of CRISPR-Cas12a (cpf1) for the Development of a Universal Electrochemical Biosensor, Angew. Chemie—Int. Ed., 58, 17399-17405, Oct. 17, 2019.

Ding, X., et al.,. Ultrasensitive and visual detection of SARS-CoV-2 using all-in-one dual CRISPR-Cas12a assay, Nat. Commun. 11, 1-10, Sep. 18, 2020.

(Continued)

*Primary Examiner* — J. Christopher Ball
(74) *Attorney, Agent, or Firm* — CANTOR COLBURN LLP

(57) ABSTRACT

Described herein is an immobilization-free, electrochemical method of detecting a target DNA sequence in a sample. The method includes: incubating the sample with a detection mixture, applying an electric field including an alternating current electric field and a direct current offset to the detection mixture to concentrate nucleic acids in the sample and the nucleic acid probe on a positively charged working electrode, wherein a Class 2 Cas protein trans-cleaved electroactive probe is released from the nucleic acid probe when the target DNA is present in the sample and diffuses toward a negatively charged electrode; and measuring the current as potential is applied, wherein detection of a current in the detection mixture indicates the presence of the target DNA sequence in the sample.

20 Claims, 18 Drawing Sheets

Specification includes a Sequence Listing.

(56) References Cited

PUBLICATIONS

Erdem, A., et al., Methylene Blue as a Novel Electrochemical Hybridization Indicator, Electroanalysis 2001, 13, 219-223, Jul. 3, 2000.

Fixe, F., et al., Electric-field assisted immobilization and hybridization of DNA oligomers on thin-film microchips, Nanotechnology 16, 2061-2071, Aug. 9, 2005.

Fixe, F., et al., Immobilization and hybridization by single submillisecond electric field pulses, for pixel-addressed DNA microarrays, Biosens. Bioelectron. 19, 1591-1597, Jan. 2004.

Gootenberg, J.S., et al., Nucleic acid detection with CRISPR-Cas13a/C2c2, Science 356, 438-442 (2017) Apr. 28, 2017.

Hajian, R., et al., Detection of unamplified target genes via CRISPR-Cas9 immobilized on a graphene field-effect transistor Nat. Biomed. Eng., 3, 427-437, Jun. 2019.

Hsieh, K., et al., Rapid, Sensitive, and Quantitative Detection of PathogenicDNAat the Point of Care through Microfluidic Electrochemical Quantitative Loop-Mediated Isothermal Amplification, Angew. Chem. Int. Ed. Apr. 4, 2012, 51, 4896-4900.

Kadimisetty, K., et al., Fully 3D printed integrated reactor array for point-of-care molecular diagnostics, Biosens. Bioelectron. 109, 156-163, Jun. 30, 2018.

Li, F., et al., An ultrasensitive CRISPR/Cas12a based electrochemical biosensor for Listeria monocytogenes detection, Biosens. Bioelectron. 179, 113073, May 2021.

Li, S.Y., et al., CRISPR-Cas12a-assisted nucleic acid detection, Cell Discov, 4:20, Apr. 24, 2018.

Ogilvie, G.S., et al., Effect of Screening With Primary Cervical HPV Testing vs Cytology Testing on High-grade Cervical Intraepithelial Neoplasia at 48 Months The HPV FOCAL Randomized Clinical Trial, JAMA—J. Am. Med. Assoc. 320, 43-52, Jul. 3, 2018.

Pänke, O., et al., Voltammetric detection of single base-pair mismatches and quantification of label-free target ssDNA using a competitive binding assay, Biosens. Bioelectron. 22, 2656-2662, Jan. 2007.

Radtkey, R., et al., Rapid, high fidelity analysis of simple sequence repeats on an electronically active DNA microchip, Nucleic Acids Res. 28, 17, Jan. 20, 2000.

Schiffman, M., et al., Human papillomavirus and cervical cancer, Lancet, vol. 370, 890-907, Sep. 8, 2007.

Shariati, M., et al., An ultrasensitive label free human papilloma virus DNA biosensor using gold nanotubes based on nanoporous polycarbonate in electrical alignment, Anal. Chim. Acta, 1048, 31-41, Feb. 7, 2019.

Sosnowski, R.G., et al., Rapid determination of single base mismatch mutations in DNA hybrids by direct electric field control, Proc. Natl. Acad. Sci. U. S. A. 94, 1119-1123, Feb. 1997.

Swami, N., et al., Enhancing DNA hybridization kinetics through constriction-based Dielectrophoresis, Lab Chip 9, 3212-3220, Aug. 2009.

Wang, R., et al., Ultrafast visual nucleic acid detection with CRISPR/Cas12a and rapid PCR in single capillary, Sensors Actuators, B Chem. 326, 128618, Jul. 26, 2020.

Wang, S., et al., Toehold Mediated One-Step Conformation-Switchable "Signal-On" Electrochemical DNA Sensing Enhanced with Homogeneous Enzymatic Amplification, Anal. Chem., 89, 5349-5356, Apr. 28, 2017.

Xiao, Y., et al., Label-Free Electrochemical Detection of DNA in Blood Serum via Target-Induced Resolution of an Electrode-Bound DNA Pseudoknot, J. Am. Chem. Soc. 129, 11896-11897, Sep. 12, 2007.

Xu, W., et al., Surpassing the detection limit and accuracy of the electrochemical DNA sensor through the application of CRISPR Cas systems, Biosens. Bioelectron., 155, 112100, May 1, 2020.

Xuan, F., et al., Conformation-Dependent Exonuclease III Activity Mediated by Metal Ions Reshuffling on Thymine-Rich DNA Duplexes for an Ultrasensitive Electrochemical Method for $Hg^{2+}$ Detection, Anal. Chem. 85, 4586-4593, Mar. 24, 2013.

Yin, K., et al., Dynamic Aqueous Multiphase Reaction System for One-Pot CRISPRCas12a-Based Ultrasensitive and Quantitative Molecular Diagnosis, Anal. Chem. 92, 8561-8568, Mar. 24, 2020.

Yu, Z., et al., A disposable electrochemical aptasensor using single-stranded DNA-methylene blue complex as signal-amplification platform for sensitive sensing of bisphenol A, Sensors Actuators, B Chem. 284, 73-80, Apr. 1, 2019.

Zhang, D., et al., CRISPR/Cas12a-Mediated Interfacial Cleaving of Hairpin DNA Reporter for Electrochemical Nucleic Acid Sensing, ACS Sensors 5, 557-562, Feb. 12, 2020.

Zhou, W., et al., A CRISPR-Cas9-triggered strand displacement amplification method for ultrasensitive DNA detection, Nat. Commun. 9, 1-11, Nov. 27, 2018.

Peterson, A.W., et al., The effect of surface probe density on DNA hybridization, Nucleic Acids Res. 29, 5163-5168, Oct. 11, 2001.

SEQUENCE LISTING

```
Sequence total quantity: 4
SEQ ID NO: 1             moltype = RNA   length = 41
FEATURE                  Location/Qualifiers
source                   1..41
                         mol_type = other RNA
                         organism = synthetic construct
SEQUENCE: 1
taatttctac taagtgtaga ttgaagtaga tatggcagca c                    41

SEQ ID NO: 2             moltype = DNA   length = 157
FEATURE                  Location/Qualifiers
source                   1..157
                         mol_type = genomic DNA
                         organism = Human Papilloma Virus-16
SEQUENCE: 2
ataatggcat tgttggggt aaccaactat ttgttactgt tgttgatact acacgcagta   60
caaatatgtc attatgtgct gccatatcta cttcagaaac tacatataaa aatactaact  120
ttaaggagta cctacgacat ggggaggaat atgattt                          157

SEQ ID NO: 3             moltype = DNA   length = 31
FEATURE                  Location/Qualifiers
source                   1..31
                         mol_type = other DNA
                         organism = synthetic construct
SEQUENCE: 3
ttgttggggt aaccaactat ttgttactgt t                                31

SEQ ID NO: 4             moltype = DNA   length = 29
FEATURE                  Location/Qualifiers
source                   1..29
                         mol_type = other DNA
                         organism = synthetic construct
SEQUENCE: 4
cctccccatg tctgaggtac tccttaaag                                   29
```

ELECTROCHEMICAL BIOSENSOR AND USES THEREOF

CROSS-REFERENCE OF RELATED APPLICATIONS

This application claims priority to and the benefit of U.S. Provisional Patent Application No. 63/222,989, filed on 17 Jul. 2021, which is incorporated by reference herein in its entirety for all purposes.

STATEMENT REGARDING FEDERALLY SPONSORED RESEARCH & DEVELOPMENT

This invention was made with government support under RO1 EB023607, R01 CA214072, and R61 AI154642 awarded by the National Institutes of Health. The government has certain rights in the invention.

INCORPORATION BY REFERENCE

In compliance with 37 C.F.R. § 1.52(e)(5), the sequence information contained in electronic file name: UCT0298US2_Sequence_Listing_13JUN2022.xml; size 4.63 KB; created on: 13 Apr. 2022; using WIPO Sequence 2.1.0, is hereby incorporated herein by reference in its entirety.

FIELD OF THE DISCLOSURE

Described herein is a method of detecting deoxyribonucleic acid targets, such as mutations, genotypes, cancers, infectious agents, pathogens, microorganisms, or nucleic acids associate with a disease, disorder, or condition.

BACKGROUND

Simple, rapid, and sensitive detection of nucleic acids plays a crucial role in early screening of cancer, infectious disease diagnostics, genotyping, and food safety monitoring. Polymerase chain reaction (PCR) methods have been widely used for nucleic acid detection due to their high sensitivity and specificity. However, PCR methods typically require bulky equipment, well-trained personnel, and long turnover times, limiting their utilization to only well-equipped laboratories. Recently, cluster regularly interspaced short palindromic repeats (CRISPR)-associated (Cas) proteins (for example, Cas9, Cas12a, Cas13a, etc.) have emerged as tools for sequence-specific nucleic acid detection. Due to their high sensitivity, specificity, and ability to be programmed, researchers are exploiting CRISPR-Cas proteins to develop various nucleic acid-based molecular diagnostic tools. For example, several research groups have combined CRISPR-Cas12a programmed by CRISPR RNA (crRNA) with isothermal amplification to specifically detect nucleic acid targets with high sensitivity. By recognition of its target deoxyribonucleic acid (DNA), Cas12a protein can be specifically activated and can indiscriminately cleave single-stranded DNA (ssDNA) (trans-cleavage activity). However, most of these methods use ssDNA labeled with both fluorophore and quencher as the fluorescence probe for fluorescence detection, which relies on relatively expensive and complicated fluorescence detectors.

Compared with fluorescence detection, electrochemical detection provides a simpler, lower cost, and more powerful strategy for nucleic acid detection. Recent efforts have established several electrochemical CRISPR-based biosensors for nucleic acid detection by taking advantage of the cleavage capabilities of CRISPR-Cas proteins. However, most of these biosensors require the electrochemical probes to be immobilized on the electrode surface, which is a complicated and time-consuming process. In addition, due to the steric hindrance of the immobilized probes, the immobilization approaches can suffer from reduced cleavage efficiency and selectivity on a heterogeneous surface compared to that in a homogeneous solution. Therefore, there is a need to develop a simple, sensitive, and versatile electrochemical CRISPR biosensing method for DNA detection without the need for a complex immobilization processing of electrochemical probes.

SUMMARY

An aspect of the present disclosure provides an immobilization-free, electrochemical method of detecting a target deoxyribonucleic nucleic acid (DNA) sequence in a sample. The method comprises: (A) incubating the sample with a detection mixture, (B) applying an electric field comprising an alternating current (AC) electric field and a direct current (DC) offset to the detection mixture (for example, after incubating the sample with the detection mixture) to concentrate nucleic acids in the sample and a nucleic acid probe on a positively charged working electrode, wherein Class 2 Cas protein trans-cleaved electroactive probe or electrochemical hybridization indicator is released from the nucleic acid probe when the target DNA sequence is present in the detection mixture (e.g., the released electroactive probe diffuses toward a negatively charged electrode), and (C) measuring, after applying the electric field, the current of the detection mixture as potential is applied (for example, measuring the current of the detection mixture as the potential is varied and/or examining the electrochemical activity of the detection mixture, after applying the electric field, via voltammetry and/or differential pulse voltammetry (DPV)), wherein detection of a current in the detection mixture indicates the presence of the target DNA sequence in the sample, wherein the detection mixture comprises, consists essentially of, or consists of: (i) a nucleic acid probe that has a negative charge and that includes a single-stranded DNA (ssDNA) sequence that hybridizes with (or that is complementary to) a nucleic acid sequence of the target DNA sequence covalently linked to an electroactive probe (or electrochemical hybridization indicator), wherein the electroactive probe (or electrochemical hybridization indicator) has a charge that is less negative than DNA (for example, an electroactive probe or electrochemical hybridization indicator that has a neutral charge or a positive charge that is no greater than the negative charge of the ssDNA sequence of the nucleic acid probe); (ii) a Class 2 cluster regularly interspaced short palindromic repeats (CRISPR)-associated (Cas) protein or enzyme that has trans-cleavage activity for ssDNA (i.e., nonspecifically cleaves ssDNA); and (iii) a guide ribonucleic acid (gRNA) or CRISPR RNA (crRNA) that includes a scaffold sequence that interacts with (or binds to) the Class 2 Cas protein and a nucleic acid sequence that hybridizes with (or that is complementary to) the target DNA sequence (e.g., hybridizes with the target DNA sequence at a different location than the nucleic acid probe).

A further aspect of the present disclosure provides a method of diagnosing an infection (e.g., Human Papillomavirus, such as via the detection of the L1 gene of Human Papillomavirus), disease, disorder, condition, or genotype (e.g., Human Papillomavirus-16 or Human Papillomavirus-18). The method comprises performing the method of detecting a target DNA sequence described herein to detect a target DNA sequence that is characteristic and/or indicative of the infection, disease, disorder, condition, or genotype.

Another aspect of the present disclosure provides a method of treating an infection (e.g., Human Papillomavirus), disease, disorder, condition, or genotype (e.g., Human Papillomavirus-16 or Human Papillomavirus-18). The method of treating comprising diagnosing an infection, disease, disorder, condition, or genotype by the methods described herein, and treating the infection, disease, disorder, condition, or genotype.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating certain embodiments of the disclosure and are not to be construed as limiting the disclosure. Further objects, features, and advantages of the disclosure will become apparent from the following detailed description taken in conjunction with the accompanying figures showing illustrative embodiments of the disclosure.

(FIG. 1A) Trans-cleavage and cis-cleavage activities of CRISPR-Cas12a protein in the presence of CRISPR RNA or guide RNA (crRNA or gRNA, respectively), DNA target, and ssDNA (non-target). (FIG. 1B) Operation procedures of the EFE, electrochemical CRISPR biosensor. (First Two Panels) A pulsed electric field is applied to attract nucleic acids (for example, electroactive ssDNA probe, dsDNA target) on the positively charged working electrode surface due to the static electric force. (Third Panel) Electrochemical detection in the absence and presence of the target DNA. The trans-cleavage activity of activated a Class 2 Cas protein with trans-cleavage activity for dsDNA (for example, Cas12a) releases less negative, e.g., MB-labeled probe, resulting in an increased electrochemical current during differential pulse voltammetry (DPV) detection.

(FIG. 3A-3D) Electrochemical current of the positive and negative samples at different ssDNA-MB probe concentrations (1, 2, 5, and 10 µM, respectively). PC is the positive control with 500 pM HPV-16 DNA target. NC is the negative control without HPV-16 DNA target. (FIG. 3E) Comparison of the electrochemical current difference at ssDNA-MB concentrations ranging from 1 µM to 10 µM. Error bars represent the means±s.d. from three replicates (n=3).

(FIG. 4A) Fluorescence images of the reaction chambers of the electrochemical CRISPR biosensor at different incubation times (0, 20, 40, and 60 minutes). (FIG. 4B) Effect of the peak-to-peak amplitude (0, 1, 10, and 100 mV) on the CRISPR-based DNA detection. (FIG. 4C) Effect of the frequency (1, 10, and 100 Hz) on the CRISPR-based DNA detection. The relative fluorescence intensities were recorded at the endpoint of the CRISPR reaction. PC is the positive control with 500 pM HPV-16 DNA target. NC is the negative control without HPV-16 DNA target. Error bars represent the means±s.d. from three replicates (n=3).

(FIG. 5A) The effect of different peak-to-peak values (Vpp) ranging from 0 to 100 mV on the CRISPR-based nucleic acid detection. (FIG. 5B) Effect of different frequency ranging from 1 to 100 Hz on the CRISPR-based nucleic acid detection.

(FIG. 6A) Statistical analysis was performed using a one-way ANOVA test with Tukey's comparison test, where n.s.=not significant with p>0.05 and the asterisks (*, , *, ****) denote significant differences with p values ($*=0.001<P\leq0.05$, $=0.0001<P\leq0.001$, $*=0.00001<P\leq0.0001$, $****=P\leq0.00001$). Error bars represent the means±s.d. from three replicates (n=3). (FIG. 6B) Real-time CRISPR florescence curves for detection of HPV-16 DNA target ranging from 1 fM to 100 nM in the reaction tubes.

(FIG. 7A) Electrochemical response curves of the EFE electrochemical CRISPR biosensor for HPV-16 DNA detection in clinical samples. (FIG. 7B) Normalized electrochemical current of the EFE electrochemical CRISPR biosensor for HPV-16 DNA detection in clinical samples. S1, S2, S4, and S5 are positive clinical samples. S3 and S6 are negative samples. PC and NC are, respectively, the positive and negative controls. Error bars represent the means±s.d. from three replicates (n=3).

(FIG. 8A) Differential pulse voltammetry (DPV) curves of electrochemical CRISPR biosensor without applying an electric field for detection of HPV-16 target ranging from 100 fM to 100 nM. (FIG. 8B) Differential pulse voltammetry curves of electrochemical CRISPR biosensor with applying an electric field for detection of HPV-16 target ranging from 100 fM to 100 nM.

(FIG. 9A) Real-time fluorescence curves of CRISPR-based fluorescence detection of HPV-16 DNA. (FIGS. 9B and 9C) Endpoint fluorescence images of CRISPR-based reaction tube in a portable transilluminator (MaestroGen Inc.) and a ChemiDoc MP Imaging System (BIO-RAD), respectively.

DETAILED DESCRIPTION

Figure 1A:
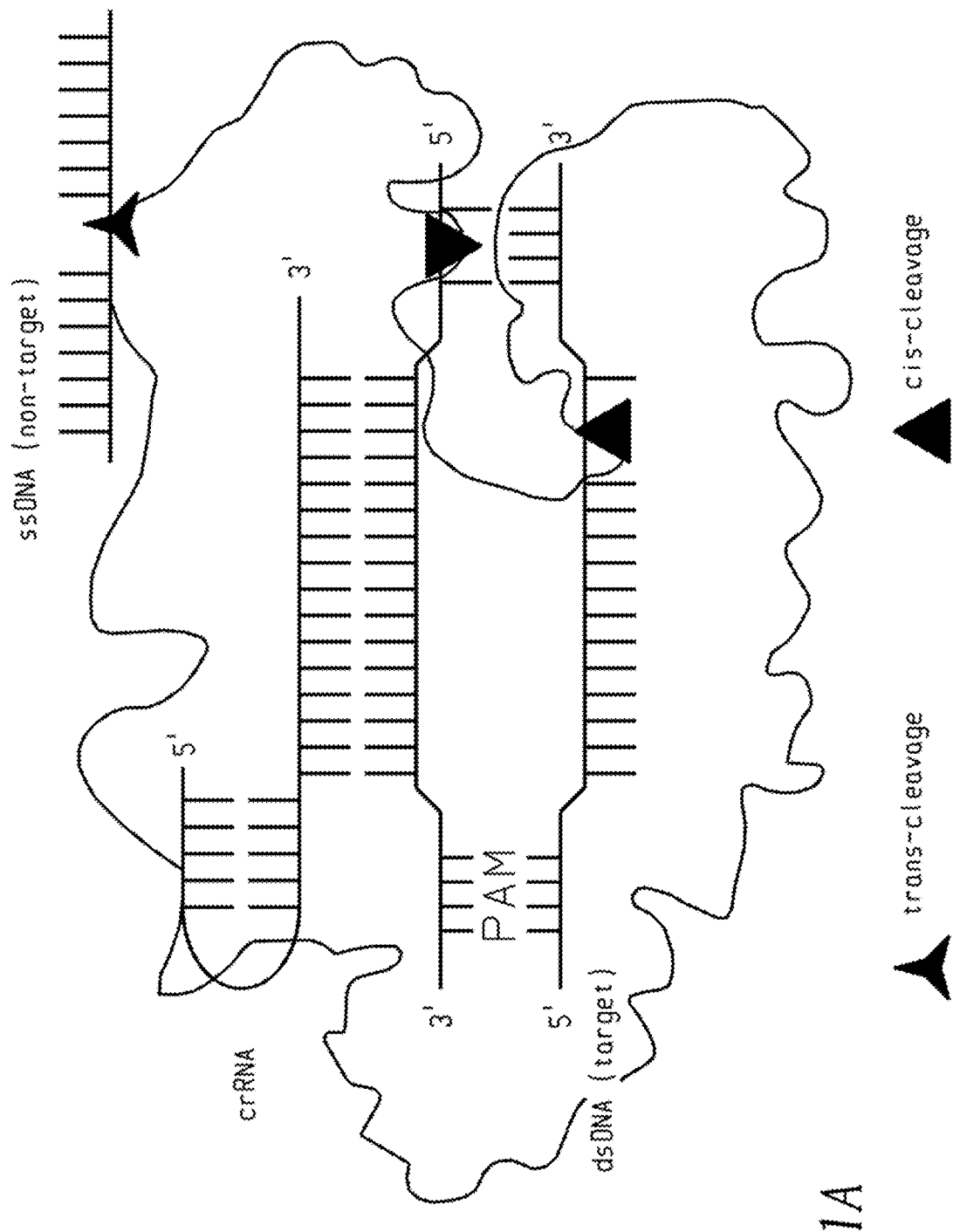
FIGS. 1A and 1B. Working principle of the electric field-enhanced (EFE), immobilization-free electrochemical cluster regularly interspaced short palindromic repeats (CRISPR) biosensor for DNA detection.

The following is a detailed description provided to aid those skilled in the art in practicing the present disclosure.

Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure. All publications, patent applications, patents, figures, and other references mentioned herein are expressly incorporated by reference in their entirety for all purposes.

The present disclosure provides an immobilization-free, electrochemical method of detecting a target deoxyribonucleic nucleic acid (DNA) sequence in a sample. Such DNA sequences may be any nucleic acid sequence that one desires to detect, such a pathogen, microorganism, infectious agent, mutation, genotype, cancer, disease, disorder, condition, etc. The methods described herein, as well as diagnostic tests and/or systems implementing the same are capable of producing highly accurate results in relatively short amounts of time without complicated methods and equipment.

The methods described herein, as well as the diagnostic tests and systems implementing the same, are highly sensitive and accurate and may be safely and easily operated or conducted by untrained individuals. As a result, the diagnostic tests, systems, and methods may be useful in a wide variety of contexts. For example, in some cases, the methods, and diagnostic tests and systems implementing the same, may be available over the counter for use by consumers. In such cases, untrained consumers may be able to self-administer the diagnostic test or system (or administer the test to friends and family members) implementing the methods described herein in their own homes (or any other location of their choosing) without the assistance of another person. In some cases, the diagnostic tests, systems, or methods may be operated or performed by employees or volunteers of an organization (e.g., a school, a medical office, a business). For example, a school (e.g., an elementary school, a high school, and/or a university) may test its students, teachers, and/or administrators, a medical office (e.g., a doctor's office, a dentist's office) may test its patients, or a business may test its employees for a particular disease. In each case, the diagnostic tests or systems implementing the methods described herein may be operated or performed by the test subjects (e.g., students, teachers, patients, and/or employees) or by designated individuals (e.g., a school nurse, a teacher, a school administrator, and/or a receptionist). Point-of-care administration is also contemplated herein, where the diagnostic tests and systems implementing the methods described herein are administered by a trained medical professional in a point-of-care setting. Certain embodiments additionally contemplate a downloadable software component or software ecosystem, which may assist with test result readout and data aggregation, as well as performing the test/method.

In some embodiments, each component of the methods described herein, and the diagnostic tests and/or systems that implement the same, is relatively small. Thus, unlike other diagnostic systems/methods that require bulky and expensive laboratory equipment (e.g., thermocyclers for PCR tests), diagnostic tests and systems that implement the methods described herein may be easily transported and/or easily stored in homes and/or businesses. Since expensive laboratory equipment can be avoided, the methods of the present disclosure may be more cost effective than conventional diagnostic methods. The accurate and convenient detection method provides a method for detection, surveillance, and/or control of any nucleic acid, especially in resource-limited settings.

It should be appreciated that while some examples of the rapid diagnostic tests, systems, and methods provided herein are discussed in the context of specific pathogens or diseases (e.g., Human Papillomavirus genotype 16), the techniques are not so limited and can be used to detect any nucleic acid, pathogen, or disease in which nucleic acid molecules characteristic to or indicative of such disease. Therefore, the examples provided herein of the various embodiments are intended for exemplary purposes only.

An aspect of the disclosure provides an immobilization-free, electrochemical method of detecting a target deoxyribonucleic acid (DNA) sequence in a sample. The method comprises: (A) incubating the sample with a detection mixture, (B) applying an electric field comprising an alternating current (AC) electric field and a direct current (DC) offset to the detection mixture (for example, after incubating the sample with the detection mixture) to concentrate nucleic acids in the sample and a nucleic acid probe on a positively charged working electrode, wherein Class 2 Cas protein trans-cleaved electroactive probe or electrochemical hybridization indicator is released from the nucleic acid probe when the target DNA sequence is present detection mixture (e.g., the released electroactive probe diffuses toward a negatively charged electrode), and (C) measuring, after applying the electric field, the current of the detection mixture as potential is applied (for example, measuring the current of the detection mixture as the potential is varied and/or examining the electrochemical activity of the detection mixture, after applying the electric field, via voltammetry and/or differential pulse voltammetry (DPV)), wherein detection of a current in the detection mixture indicates the presence of the target DNA sequence in the sample, wherein the detection mixture comprises, consists essentially of, or consists of: (i) a nucleic acid probe that has a negative charge and that includes a single-stranded DNA (ssDNA) sequence that hybridizes with (or that is complementary to) a nucleic acid sequence of the target DNA sequence covalently linked to an electroactive probe (or electrochemical hybridization indicator), wherein the electroactive probe (or electrochemical hybridization indicator) has a charge that is less negative than DNA (for example, an electroactive probe or electrochemical hybridization indicator that has a neutral charge or a positive charge that is no greater than the negative charge of the ssDNA sequence of the nucleic acid probe); (ii) a Class 2 cluster regularly interspaced short palindromic repeats (CRISPR)-associated (Cas) protein or enzyme that has trans-cleavage activity for ssDNA (i.e., nonspecifically cleaves ssDNA); and (iii) a guide ribonucleic acid (gRNA) or CRISPR RNA (crRNA) that includes a scaffold sequence that interacts with (or binds to) the Class 2 Cas protein and a nucleic acid sequence that hybridizes with (or that is complementary to) the target DNA sequence (e.g., hybridizes with the target DNA sequence at a different location than the nucleic acid probe). In any aspect or embodiment described herein, the gRNA includes or is CRISPR RNA (crRNA).

In any aspect or embodiment described herein, the method further comprises, prior to incubating the sample with the detection mixture, amplifying the target DNA sequence in the sample, wherein the sample incubated with the detection mixture is the amplification product (also known as amplicons), or a portion thereof. In any aspect or embodiment described herein, the method further comprises, while incubating the sample with the detection mixture, amplifying the target DNA sequence in the sample, wherein the sample incubated with the detection mixture is the amplification product or amplicons, or a portion thereof.

Thus, the present disclosure provides an immobilization-free, electrochemical method of detecting a target deoxyribonucleic nucleic acid (DNA) sequence in a sample with an amplification step. The method comprises: (A) amplifying the target DNA sequence in the sample; (B) incubating the amplification product or amplicon, or a portion thereof, with a detection mixture; (C) applying an electric field comprising an alternating current (AC) electric field and a direct current (DC) offset to the detection mixture (for example, after incubating the sample with the detection mixture) to concentrate nucleic acids in the sample and a nucleic acid probe on a positively charged working electrode, wherein Class 2 Cas protein trans-cleaved electroactive probe or electrochemical hybridization indicator is released from the nucleic acid probe when the target DNA sequence is present in the detection mixture (e.g., the released electroactive probe diffuses toward a negatively charged electrode), and (D) measuring, after applying the electric field, the current of the detection mixture as potential is applied (for example, measuring the current of the detection mixture as the potential is varied and/or examining the electrochemical activity of the detection mixture, after applying the electric field, via voltammetry and/or differential pulse voltammetry (DPV)), wherein detection of a current in the detection mixture indicates the presence of the target DNA sequence in the sample, wherein the detection mixture comprises, consists essentially of, or consists of: (i) the amplification product (or amplicons or a portion thereof (ii) a nucleic acid probe that has a negative charge and that includes a single-stranded DNA (ssDNA) sequence that hybridizes with (or that is complementary to) a nucleic acid sequence of the target DNA sequence covalently linked to an electroactive probe (or electrochemical hybridization indicator), wherein the electroactive probe (or electrochemical hybridization indicator) has a charge that is less negative than DNA (for example, an electroactive probe or electrochemical hybridization indicator that has a neutral charge or a positive charge that is no greater than the negative charge of the ssDNA sequence of the nucleic acid probe); (iii) a Class 2 cluster regularly interspaced short palindromic repeats (CRISPR)-associated (Cas) protein or enzyme that has trans-cleavage activity for ssDNA (i.e., nonspecifically cleaves ssDNA); and (iv) a guide ribonucleic acid (gRNA) or CRISPR RNA (crRNA) that includes a scaffold sequence that interacts with (or binds to) the Class 2 Cas protein and a nucleic acid sequence that hybridizes with (or that is complementary to) the target DNA sequence (e.g., hybridizes with the target DNA sequence at a different location than the nucleic acid probe).

By way of further example, the present disclosure provides an immobilization-free, electrochemical method of detecting a target deoxyribonucleic acid (DNA) sequence in a sample with an amplification step. The method comprises: (A) amplifying the target DNA sequence in the sample with a detection mixture; (B) applying an electric field comprising an alternating current (AC) electric field and a direct current (DC) offset to the detection mixture (for example, after incubating the sample with the detection mixture) to concentrate nucleic acids in the sample and a nucleic acid probe on a positively charged working electrode, wherein Class 2 Cas protein trans-cleaved electroactive probe or electrochemical hybridization indicator is released from the nucleic acid probe when the target DNA sequence is present in the detection mixture (e.g., the released electroactive probe diffuses toward a negatively charged electrode), and (C) measuring, after applying the electric field, the current of the detection mixture as potential is applied (for example, measuring the current of the detection mixture as the potential is varied and/or examining the electrochemical activity of the detection mixture, after applying the electric field, via voltammetry and/or differential pulse voltammetry (DPV)), wherein detection of a current in the detection mixture indicates the presence of the target DNA sequence in the sample, wherein the detection mixture comprises, consists essentially of, or consists of: (i) reagents to amplify the target DNA sequence; (ii) a nucleic acid probe that has a negative charge and that includes a single-stranded DNA (ssDNA) sequence that hybridizes with (or that is complementary to) a nucleic acid sequence of the target DNA sequence covalently linked to an electroactive probe (or electrochemical hybridization indicator), wherein the electroactive probe (or electrochemical hybridization indicator) has a charge that is less negative than DNA (for example, an electroactive probe or electrochemical hybridization indicator that has a neutral charge or a positive charge that is no greater than the negative charge of the ssDNA sequence of the nucleic acid probe); (iii) a Class 2 cluster regularly interspaced short palindromic repeats (CRISPR)-associated (Cas) protein or enzyme that has trans-cleavage activity for ssDNA (i.e., nonspecifically cleaves ssDNA); and (iv) a guide ribonucleic acid (gRNA) or CRISPR RNA (crRNA) that includes a scaffold sequence that interacts with (or binds to) the Class 2 Cas protein and a nucleic acid sequence that hybridizes with (or that is complementary to) the target DNA sequence (e.g., hybridizes with the target DNA sequence at a different location than the nucleic acid probe).

The present disclosure further describes methods of diagnosing an infection (e.g., Human Papillomavirus, such as via the detection of the L1 gene of Human Papillomavirus), disease, disorder, condition, or genotype (e.g., Human Papillomavirus genotype 16 or Human Papillomavirus genotype 18), the method comprising performing the method of detecting a target DNA sequence described herein to detect a target DNA sequence that is characteristic and/or indicative of the infection, disease, disorder, condition, or genotype.

The present disclosure additionally provides methods of treating an infection (e.g., Human Papillomavirus), disease, disorder, condition, or genotype (e.g., Human Papillomavirus genotype 16 or Human Papillomavirus genotype 18). The method of treating comprising diagnosing an infection, disease, disorder, condition, or genotype by the methods described herein, and treating the infection, disease, disorder, condition, or genotype.

In an aspect of present disclosure, the methods of the present disclosure are applied to a subject who is suspected of having a pathogenic infection, disease, disorder, or condition, but who has not yet been diagnosed as having such an infection, disease, disorder, or condition. A subject may be "suspected of having" a pathogenic infection, disease, disorder, or condition when the subject exhibits one or more signs or symptoms of such infection, disease, disorder, or condition. Such signs or symptoms are well known in the art and may vary, depending on the nature of the pathogen, disease, disorder, or condition, and the subject. Signs and symptoms of an infection may generally include any one or more of the following: fever, chills, cough (e.g., dry cough), generalized fatigue, sore throat, runny nose, nasal congestion, muscle aches, difficulty breathing (shortness of breath), congestion, runny nose, headaches, nausea, vomiting, diarrhea, loss of smell and/or taste, skin lesions (e.g., pox), or loss of appetite. Other signs or symptoms of an infection, disease, disorder, or condition are specifically contemplated herein. A subject may also be "suspected of having" a pathogenic infection, disease, disorder, or condition despite exhibiting no signs or symptoms of such an infection or disease (e.g., the subject is asymptomatic).

In any aspect or embodiment described herein, the methods disclosed herein are directed to detecting the presence of one or more pathogens, microorganism, or infectious agents in a sample, such as a biological sample obtained from a subject. In any aspect or embodiment described herein, the pathogen, microorganism, or infectious may be a bacterium, a fungus, a yeast, a protozoan, a parasite, or a virus. Accordingly, the methods disclosed herein can be adapted for use in other methods (or in combination) with other methods that require quick identification of pathogen, microorganism, or infectious agent species, monitoring the presence of proteins (antigens) of the pathogen/microorganism/infectious agent, antibodies, antibody genes, detection of certain phenotypes (e.g., bacterial resistance or antiviral resistance), monitoring of disease progression and/or outbreak, and antibiotic or antiviral screening. Because of the rapid and sensitive diagnostic capabilities of the embodiments disclosed here, detection of pathogen/microorganism/infectious agent species type, down to a single nucleotide difference, and the ability to be deployed as a POC device, the embodiments disclosed herein may be used to guide therapeutic regimens, such as selection of the appropriate antibiotic, antiviral, antifungal, antiparasitic, etc.

In any aspect or embodiment described herein, the methods are used to screen environmental samples (air, water, surfaces, food etc.) for the presence of, e.g., microbial contamination.

In any aspect or embodiment described herein, the method further comprises preparing the sample or set of samples for detecting the target DNA sequence in each sample (e.g., performing reverse transcriptase on an RNA sample), and optionally a positive and/or negative control.

In any aspect or embodiment described herein, the hybridization of the gDNA (or crDNA) and the target nucleic acid sequence promotes the formation of a CRISPR complex.

In any aspect or embodiment described herein, the CRISPR complex cleaves dsDNA that includes the nucleic acid probe hybridized to the nucleic acid sequence of interest, releasing the electroactive probe.

In any aspect or embodiment described herein, the method is performed in a reaction chamber of an electrochemical sensor.

In any aspect or embodiment described herein, the method is performed in a solution phase (e.g., a single solution phase).

In any aspect or embodiment described herein, the method is performed in an homogeneous solution.

In any aspect or embodiment described herein, measuring, after applying the electric field, the current of the detection mixture as potential is applied includes measuring the current of the detection mixture as the potential is varied. In any aspect or embodiment described herein, measuring, after applying the electric field, the current of the detection mixture as potential is applied includes examining the electrochemical activity of the detection mixture, after applying the electric field, via voltammetry and/or differential pulse voltammetry (DPV).

In any aspect or embodiment described herein, incubating the samples with a detection mixture includes incubating at about 35° C. to about 42° C. For example, any aspect or embodiment described herein, incubating the samples with a detection mixture includes incubating at about 35° C. to about 40° C., about 37° C., incubating at a temperature that denatures double-stranded DNA (dsDNA), and/or incubating at a temperature that separates the two strands of dsDNA that includes the target DNA sequence.

In any aspect or embodiment described herein, incubating the samples with the detection mixture is performed for about 10 to about 90 minutes. For example, in any aspect or embodiment described herein, incubating the samples with the detection mixture is performed for about 30 minutes to about 90 minutes, about 40 minutes to about 80 minutes, about 45 minutes to about 75 minutes, or about 50 minutes to about 70 minutes.

In any aspect or embodiment described herein, the detection mixture may further comprise reagents for cell lysis.

Class 2 Cas Protein and Guide RNA

In any aspect or embodiment described herein, the Class 2 CRISPR/Cas, such as Cas12a or Cpf1, subtype V-A, is capable of nonspecific cleavage of ssDNA (single-stranded DNA) and RNA which does not require a PAM (protospacer adjacent motif) recognition site, in addition to successful gene editing (cis-cleavage) at a recognized target site (requires PAM recognition). This attribute, known as trans-cleavage or collateral cleavage, is only activated once bound to an activator (ssDNA or dsDNA) that has complementary base-pairing to a crRNA or gRNA. The crRNA for Cas12a does not require tracrRNA. Guide RNA for Cas12a is often referred to as crRNA since there is no tracrRNA. By providing gRNA specific for the chosen target, hybridization of the gRNA with the specific target DNA sequence, activated the trans-cleavage activity of Class 2 Cas protein (for example, Cas12a), resulting in cleavage of the collateral ssDNA, which is labeled with the electroactive probe or electrochemical hybridization indicator, for example methylene blue. Other CRISPR/Cas enzymes that possess the trans-cleavage activity can be used in the claimed method including Cas13b (for example, C2c2, subtype VI), Cas13a, Cas12a (e.g. FnCas12a from *Francisella novicida*, LbCas12a from Lachnospiraceae bacterium, and AsCas12a from *Acidaminococcus* sp.), as well as homologs and orthologs thereof, as well as variants of Cas12a and Cas13a/b that are still capable of trans-cleavage. A "homolog" of a protein as used herein is a protein of the same species which performs the same or a similar function as the protein it is a homolog of. Homologous proteins may be but need not be structurally related or are only partially structurally related. An "ortholog" of a protein as used herein is a protein of a different species which performs the same or a similar function as the protein it is an ortholog of. Orthologous proteins may but need not be structurally related or are only partially structurally related.

In any aspect or embodiment described herein, the concentration of the Class 2 Cas protein or enzyme is at least 100 nM, at least 120 nM, at least 140, at least 160 nM, at least 180 nM, at least 200 nM, at least 220 nM, at least 240 nM, at least 250 nM, at least 260 nM. In any aspect or embodiment described herein, the concentration of the Class 2 Cas protein or enzyme is up to 200 nM, up to 220 nM, up to 240 nM, up to 250 nM, up to 260 nM, up to 280 nM, or up to 300 nM. In any aspect or embodiment described therein, the concentration of the Class 2 Cas protein or enzyme is in a any combination of the above recited concentrations, such as about 100 nM to about 300 nM or about 150 nM to about 250 nM.

In any aspect or embodiment described herein, the Class 2 Cas protein is Cas12a (for example, Cpf1, subtype V-A).

In any aspect or embodiment described herein, Class 2 Cas protein trans-cleaved electroactive probe is released from the nucleic acid probe and diffuses toward a negatively charged electrode and/or away from the positive charged electrode when the target DNA sequence is present.

In any aspect or embodiment described herein, a Cas protein or enzyme nonspecifically cleaves ssDNA (that is, has trans-cleavage activity for ssDNA).

As mentioned above, Class 2 Cas protein (e.g., Cas12a) detection of a chosen target DNA sequence and activation of the trans-cleavage activity require a gRNA, which includes or is a crRNA, a small guide molecule that can guide the Class 2 Cas protein to a specific target DNA sequence and activate Class 2 Cas protein cleavage activity. In any aspect or embodiment described herein, the gRNA includes trans-activating CRISPR RNA (tracrRNA). In any aspect or embodiment described herein, the gRNA does not include tracrRNA. In any aspect or embodiment described herein, the gRNA is a crRNA. The "target nucleic acid sequence" refers to a sequence to which a guide sequence is designed to have complementarity, where hybridization between a target sequence and a guide sequence promotes the formation of a CRISPR complex. A target sequence may comprise RNA or DNA polynucleotides. In other words, the target DNA sequence may be an RNA or DNA polynucleotide or a part of a RNA or DNA polynucleotide to which a part of the gRNA, i.e., the guide sequence, is designed to have complementarity and to which the effector function mediated by the complex comprising CRISPR effector protein and a gRNA is to be directed.

As used herein, the term "guide sequence," "crRNA," "guide RNA," or "gRNA" refers to a polynucleotide comprising any polynucleotide sequence having sufficient complementarity with a target DNA sequence to hybridize with the target DNA sequence and to direct sequence-specific binding of an RNA-targeting complex comprising the guide sequence and a CRISPR effector protein to the target DNA sequence. In any aspect or embodiment described herein, the degree of complementarity, when optimally aligned using a suitable alignment algorithm, is about or more than about 50%, 60%, 75%, 80%, 85%, 90%, 91%, 92%, 93%, 94%, 95%, 96%, 97%, 97.5%, 98%, 99%, or more, such as 100%. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, basic local alignment search tool (BLAST)-like alignment tool (BLAT), Novoalign (Novocraft Technologies; available at novocraft.com), Mapping and Assembly with Quality (ELAND; Illumina, San Diego, Calif.), Short Oligonucleotide Analysis Package (SOAP; Beijing Genomics Institute, Shenzhen, Guangdong, China), and Mapping and Assembly with Quality (Maq; SourceForge.net, San Diego, CA). The ability of a guide sequence (gRNA or crRNA) to direct sequence-specific binding of a nucleic acid-targeting complex to a target DNA sequence may be assessed by any suitable assay. For example, cleavage of a target DNA sequence may be evaluated in a test tube by providing the target DNA sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide may be selected to target any target nucleic acid sequence.

In any aspect or embodiment described herein, a gRNA (such as crRNA) or analogous polynucleotide comprising a guide sequence, is an RNA, a DNA, or a mixture of RNA and DNA, and/or wherein the polynucleotide comprises one or more modified nucleotide. As used herein, a "modified nucleotide" may refer to a nucleotide comprising a base such as, for example, adenine, guanine, cytosine, thymine, uracil, xanthine, inosine, and/or queuosine that may have been modified by the replacement or addition of one or more atoms or groups. For example, the modification may comprise a nucleotide that is modified with respect to the base moiety, such as a/an alkylated, halogenated, thiolated, aminated, amidated, or acetylated base, in various combinations. Modified nucleotides also may include nucleotides that comprise a sugar moiety modification (e.g., 2'-fluoro or 2'-O-methyl nucleotides), as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

In any aspect or embodiment described herein, the gRNA (such as, a crRNA) can comprise any structure, including but not limited to a structure of a native crRNA. The gRNA or crRNA can comprise a bulge, a hairpin, or a stem loop, preferably a single stem loop. In any aspect or embodiment described herein, a gRNA pr crRNA is about or more than about 5, 10, 15, 20, 25, 30, 35, 40, 45, 50, 75, or more nucleotides in length. In any aspect or embodiment described herein, a gRNA (such as, a crRNA) is less than about 75, 50, 45, 40, 35, 30, 25, 20, 15, 12, or fewer nucleotides in length. Preferably the gRNA (such as, a crRNA) is 10 to 30 nucleotides long. The gRNA may be synthesized using any method known in the art. For example, in some embodiments, an artificial gRNA may be synthesized by chemical synthesis, genetic engineering techniques, and/or artificial manipulation of isolated segments of nucleic acids. Exemplary gRNA for the L1 gene of HPV-16 in Table 1. In any aspect or embodiment described herein, the concentration of the gRNA or crRNA is at least 40 nM, at least 60 nM, at least 80 nM, at least 100 nM, at least 120 nM, at least 140, at least 160 nM, at least 180 nM, at least 200 nM, at least 220 nM, at least 240 nM, at least 250 nM, at least 260 nM. In any aspect or embodiment described herein, the concentration of the gRNA or crRNA is up to 100 nM, up to 120 nM, up to 140, up to 160 nM, up to 180 nM, up to 200 nM, up to 220 nM, up to 240 nM, up to 250 nM, up to 260 nM, up to 280 nM, up to 300 nM, up to 320 nM, up to 340 nM, or up to 350 nM. In any aspect or embodiment described therein, the concentration of the gRNA or crRNA is in any combination of the above recited concentrations, such as about 40 nM to about 350 nM or about 200 nM to about 300 nM.

In any aspect or embodiment described herein, the nucleic acid sequence of the guide RNA (gRNA) or crRNA that hybridizes with the target DNA sequence is complementary to the target DNA sequence, such as to a different location than that of the acid probe.

In any aspect or embodiment described herein, the gRNA or crRNA that includes a scaffold sequence that interacts with or binds to the Class 2 Cas protein and a nucleic acid sequence that hybridizes with (or that is complementary to) the target DNA sequence at a different location than the nucleic acid probe.

In any aspect or embodiment described herein, the ssDNA sequence of the gRNA or crRNA that hybridizes with or that is complementary to the target DNA sequence is about 15 base pairs to about 30 base pairs long. For example, in any aspect or embodiment described herein, the ssDNA sequence of the gRNA or crRNA that hybridizes with or that is complementary to the target DNA sequence is about 20 to about 25 base pairs. In any aspect or embodiment described herein, the ssDNA sequence of the gRNA or crRNA that hybridizes with or that is complementary to the target DNA sequence is about 21 to about 24 base pairs long.

In any aspect or embodiment described herein, the gRNA is about 35 to about 50 base pairs long. For example, any aspect or embodiment described herein, the gRNA is about 35 to about 45 base pairs or about 40 to about 45 base pairs long.

Nucleic Acid Probe

As mentioned above, the gRNA activated Class 2 Cas protein can nonspecifically trans-cleave a ssDNA probe. In any aspect or embodiment described herein, the ssDNA sequence of the nucleic acid probe is labeled with a reporter—i.e., an electroactive probe or electrochemical hybridization indicator. Additionally, the reported is covalently attached to the nucleic acid sequence of the nucleic acid probe that hybridizes with the target DNA such that when the ssDNA is cleaved by the Class 2 Cas protein or enzyme the solution is able to conduct current/electricity, which is detectable and thus indicates that the target DNA sequence is present (for example, present in the sample). Electroactive probes or electrochemical hybridization indicators, as well as methods for labeling nucleic acids with the same, are known in the art.

In any aspect or embodiment described herein, the non-specific ssDNA probe can be any oligonucleotide of any length which when cleaved can produce a detectable signal. In some embodiments, the ssDNA probe is a short oligonucleotide of about 2, 3, 4, or 5 nucleotides or more in length. In any aspect or embodiment described herein, the concentration of the nucleic acid probe is at least 0.2 µM, at least 0.5 µM, at least 0.75 µM, or at least 1.0 µM. In any aspect or embodiment described herein, the concentration of the nucleic acid probe is up to 2.0 µM, up to 1.75 µM, up to 1.5 µM, or up to 1.25 µM. In any aspect or embodiment described herein, the concentration of the probe is about 0.2 µM to about 2.0 µM, about 0.2 µM to about 1.75 µM, about 0.2 µM to about 1.5 µM, about 0.2 µM to about 1.25 µM, about 0.2 µM to about 1.0 µM, about 0.5 µM to about 2.0 µM, about 0.5 µM to about 1.75 µM, about 0.5 µM to about 1.5 µM, about 0.5 µM to about 1.0 µM, about 0.75 µM to about 2.0 µM, about 0.75 µM to about 1.75 µM, about 0.75 µM to about 1.5 µM, about 0.75 µM to about 1.25 µM, about 1.0 µM to about 2.0 µM, about 1.0 µM to about 1.75 µM, about 1.0 µM to about 1.5 µM, about 1.25 µM to about 2.0 µM, about 1.25 µM to about 1.75 µM, or about 1.50 µM to about 2.0 µM.

In any aspect or embodiment described herein, the ssDNA sequence of the nucleic acid probe that hybridizes with or that is complementary to a nucleic acid sequence of the target DNA sequence is about 4 base pairs to about 20 base pairs long. For example, any aspect or embodiment described herein, the nucleic acid sequence of the nucleic acid probe that hybridizes with or that is complementary to a nucleic acid sequence of the target DNA sequence is about 4 to about 15 base pairs or about 4 to about 10 base pairs long.

In any aspect or embodiment described herein, the ssDNA sequence of the nucleic acid probe that hybridizes with a nucleic acid sequence of the target DNA sequence is complementary to a nucleic acid sequence of the target DNA sequence.

The terms "electroactive probe" and "electrochemical hybridization indicator" are used herein interchangeably to refer to a probe or indicator that generates electrochemical current in a solution, such as an aqueous solution.

In any aspect or embodiment described herein, the electroactive probe or electrochemical hybridization indicator has a neutral charge. In any aspect or embodiment described herein, the electroactive probe or electrochemical hybridization indicator has a positive charge. In any aspect or embodiment described herein, the electroactive probe or electrochemical hybridization indicator has a positive charge that is no greater than the negative charge of the ssDNA sequence of the nucleic acid probe.

In any aspect or embodiment described herein, the electroactive probe is located on the 5' end of the ssDNA sequence that hybridizes with (or that is complimentary to) a nucleic acid sequence of the target DNA sequence.

In any aspect or embodiment described herein, the electroactive probe is located on the 3' end of the ssDNA sequence that hybridizes with (or that is complimentary to) a nucleic acid sequence of the target DNA sequence.

In any aspect or embodiment described herein, the nucleic acid probe has an electroactive probe located on the 5' end of the ssDNA sequence that hybridizes with (or that is complimentary to) a nucleic acid sequence of the target DNA sequence and has an electroactive probe located on the 3' end of the ssDNA sequence that hybridizes with (or that is complimentary to) a nucleic acid sequence of the target DNA sequence.

In any aspect or embodiment described herein, the electroactive probe is methylene blue.

Electric Field

In any aspect or embodiment described herein, applying an electric field is performed after incubating the sample with the detection mixture.

In any aspect or embodiment described herein, the electric field is applied for about 10 to about 90 minutes while or prior to measuring the current of the detection mixture. For example, in any aspect or embodiment described herein, the electric field is applied for about 30 to about 90 minutes, about 40 minutes to about 80 minutes, about 45 minutes to about 75 minutes, or about 50 minutes to about 70 minutes while or prior to measuring the current of the detection mixture.

In any aspect or embodiment described herein, the electric potential or peak-to-peak potential (Vpp) of the AC electric field is about 0.1 millivolts (mV) to about 100 mV. For example, in any aspect or embodiment described herein, the electric potential or peak-to-peak potential (Vpp) of the AC electric field is about 0.1 mV to about 50 mV or about 0.5 mV to about 25 mV.

In any aspect or embodiment described herein, the electric potential of the DC offset or Offset is about 0.10% to about 90% of the electric potential of the electric potential or Vpp of the AC electric field. For example, in any aspect or embodiment described herein, the electric potential of the DC offset or Offset is about 0.25% to about 75%, about 35% to about 65%, about 40% to about 60%, or about 50% of the electric potential or Vpp the electric potential of the AC electric field.

In any aspect or embodiment described herein, the frequency (f) of the electric field is about 1 hertz (Hz) to about 100 Hz. For example, in any aspect or embodiment described herein, the frequency (f) of the electric field is about 1 hertz (Hz) to about 100 Hz. For example, the frequency (f) of the electric field is about 1 Hz to about 100 Hz, about 1 Hz to about 90 Hz, about 1 Hz to about 80 Hz, about 1 Hz to about 70 Hz, about 1 Hz to about 60 Hz, about 1 Hz to about 50 Hz, about 1 Hz to about 40 Hz, about 10 Hz to about 100 Hz, about 10 Hz to about 90 Hz, about 10 Hz to about 80 Hz, about 10 hertz Hz to about 70 Hz, about 10 Hz to about 60 Hz, about 10 Hz to about 50 Hz, about 20 Hz to about 100 Hz, about 20 Hz to about 90 Hz, about 20 Hz to about 80 Hz, about 20 hertz Hz to about 70 Hz, about 30 Hz to about 100 Hz, about 30 Hz to about 90 Hz, about 30 Hz to about 80 Hz, about 40 Hz to about 100 Hz, about 40 Hz to about 90 Hz, or about 50 Hz to about 100 Hz.

In any aspect or embodiment described herein, the period of the electric field (T) (that is, the AC electric field and the DC offset) is about (0.05×f) to about (2.0×f). For example, in any aspect or embodiment described herein, the period of the electric field (T) is about (0.07×f) to about (1.0×f) or about (0.1×f). For example, the period of the electric field (T) is about (0.05×f) to about (2.0×f), about (0.05×f) to about (1.5×f), about (0.05×f) to about (1.0×f), about (0.05×f) to about (0.5×f), about (0.1×f) to about (2.0×f), about (0.1×f) to about (1.5×f), about (0.1×f) to about (1.0×f), about (0.1×f) to about (0.5×f), about (0.5×f) to about (2.0×f), about (0.5×f) to about (1.5×f), about (0.5×f) to about (1.0×f), about (1.0×f) to about (2.0×f), about (1.0×f) to about (1.5×f), or about (1.5×f) to about (2.0×f).

In any aspect or embodiment described herein, the electric field has a pulse width (i.e., p or the pulse width of the AC electric field) that is about (0.10×T) to about (0.95×T). For example, in any aspect or embodiment described herein, the electric field has a pulse width that is about (0.25×T) to about (0.95×T), about (0.40×T) to about (0.75×T), or about (0.5×T). For example, the electric field has a pulse width that is about (0.10×T) to about (0.95×T), about (0.10×T) to about (0.75×T), about (0.10×T) to about (0.50×T), about (0.10×T) to about (0.35×T), about (0.25×T) to about (0.95×T), about (0.25×T) to about (0.75×T), about (0.25×T) to about (0.50×T), about (0.50×T) to about (0.95×T), about (0.50×T) to about (0.75×T), or about (0.75×T) to about (0.95×T).

Target Deoxyribonucleic Acid (DNA) and Sample

A sample can be from any patient specimen or body fluid including, but not limited to, urine, sputum, respiratory washes, nasal and other respiratory specimens, cell scrapings or swab from the mouth or interior cheek, exhaled breath particles, blood, plasma, saliva, amniotic fluid, vaginal and anal swabs, culture media (e.g. liquid in which a cell, such as a pathogen cell, has been grown), surgical biopsy specimens, organ tissues (skin, lymphatic nodes, liver, lungs, stomach, kidney, etc.), as well as animal and plant products (eggs, shrimps, rice, milk, fruit, etc.).

In any aspect or embodiment described herein, sample preparation (such as, clinical sample preparation) includes cell lysis in order to open or lyse a cell to release the nucleic acids of the cell. Exemplary cell lysis reagents include, but is not limited to, a detergent, a salt as described herein, such as NaCl, KCl, ammonium sulfate, or others. Detergents that may be appropriate for the methods described herein may include Triton X-100, sodium dodecyl sulfate (SDS), CHAPS (3-[(3-cholamidopropyl)dimethylammonio]-1-propanesulfonate), ethyl tri methyl ammonium bromide, nonyl phenoxypolyethoxylethanol (NP-40). Concentrations of detergents may depend on the particular application and may be specific to the reaction in some cases.

In any aspect or embodiment described herein, the sample examined in the methods described herein is a crude extract of a sample comprising cells.

In any aspect or embodiment described herein, the method comprises preparing a sample comprising cells, which includes extracting the target DNA sequence. In any aspect or embodiment described herein, preparing the sample further includes concentrating the target DNA sequence. In any aspect or embodiment described herein, preparing the sample further includes removing potential inhibitors of detection and/or amplification from the extract. Methods for isolation of nucleic acids from biological samples are known.

In any aspect or embodiment described herein, the target DNA sequence is a positive control nucleic acid sequence (e.g., a housekeeping gene that regulates basic cellular functions and displays highly uniform expression). A positive control is a control group that is known to produce results, for example a solution known to contain the target DNA sequence, which confirms the correctness of the test. Frequently used housekeeping genes in mammalian cells are known in the art and include actin, glyceraldehyde 3-phosphate (GAPDH), ubiquitin, beta-tubulin, ribonuclease P RNA (RNase P) component H1, telomerase reverse transcriptase, to name a few. For example, in any aspect or embodiment described herein, the positive control is the human RNase P (RP) gene.

The failure to detect a positive control may indicate one or more of the following: improper specimen collection resulting in the lack of sufficient sample material in the diagnostic assay, improper extraction of nucleic acids from clinical materials resulting in loss of nucleic acids and/or nucleic acid degradation, improper assay set up and execution, and/or reagent or equipment malfunction. Thus, successful detection of the positive control indicates successful collection, extraction (if applicable), amplification (if applicable), and Cas protein cleavage activity of nucleic acids from the sample. A positive result on the positive control indicates that the user successfully obtained the sample material, the lysis and extraction (if applicable) steps were completed effectively, and the Cas protein cleavage was effective in the sample. In instances where the positive control is detected, the test is valid.

In any aspect or embodiment described herein, the target DNA sequence is a negative control nucleic acid sequence. A negative control is a control group that is not expected to produce results, for example, a solution known to be free of the target DNA sequence.

In any aspect or embodiment described herein, the target DNA sequence is a nucleic acid sequence from at least one of a mutation, genotype, cancer, a disease/disorder/condition associated with the target DNA sequence, infectious agent, pathogen, microorganism, or a combination thereof. In any aspect or embodiment described herein, the target DNA sequence is a nucleic acid sequence from at least one of a bacteria, virus, fungi, viroid, protozoa, parasite, or a combination thereof. In choosing a nucleic acid sequence that hybridize or that is complimentary to the target DNA sequence, nucleic acid sequences from pathogen, infectious agent, and microorganism genes can be selected from regions known to maximize inclusivity across known strains, genotypes, etc., and/or minimize cross-reactivity with related pathogens, infection agents, microorganisms, and/or genomes likely to be present in the sample. Similarly, in choosing a nucleic acid sequence that hybridize or that is complimentary to the target DNA sequence, nucleic acid sequence for a mutation, cancer, genotype, pathogen, infectious organism, or microorganism, disease, disorder, or condition nucleic acids can be selected from regions to minimize cross-reactivity with non-target DNA sequences (such as, those likely to be present in the sample) and/or maximizes the inclusivity across known sequences that are characteristic or indicative of a mutation, cancer, genotype, pathogen, infectious organism, or microorganism, disease, disorder, or condition.

In any aspect or embedment described herein, the target DNA sequence is derived from a ribonucleic acid (RNA) sequence. For example, in any aspect or embodiment described herein, the method further comprises performing (e.g., performing prior to incubating and/or prior to amplifying the target DNA sequence) a reverse transcription reaction to produce the target DNA sequence from a RNA sequence.

For example, in any aspect or embodiment described herein, when the method further comprises performing a reserves transcription reaction, the RNA sequence is a positive control nucleic acid sequence, or the RNA sequence is a nucleic acid sequence from at least one of a mutation, genotype, cancer, a disease/disorder/condition associated with the RNA sequence, infectious agent, pathogen, microorganism, or a combination thereof. For example, in any aspect or embodiment described herein, the RNA sequence is a nucleic acid sequence from at least one of a bacteria, virus, fungi, protozoa, viroid, parasite, or a combination thereof.

The following provides an example list of the types of infectious agents, pathogens, and/or microbes that might be detected using the embodiments disclosed herein.

Bacteria

In any aspect or embodiment described herein, the infectious agent, pathogen, and/or microbe is a bacterium. Examples of bacteria that can be detected in accordance with the disclosed methods include without limitation any one or more of (or any combination of) *Acinetobacter baumanii*, *Actinobacillus* sp., *Actinomycetes*, *Actinomyces* sp. (such as *Actinomyces israelii* and *Actinomyces naeslundii*), *Aeromonas* sp. (such as *Aeromonas hydrophila*, *Aeromonas veronii biovar sobria* (*Aeromonas sobria*), and *Aeromonas caviae*), *Anaplasma phagocytophilum*, *Anaplasma marginale Alcaligenes xylosoxidans*, *Acinetobacter baumannii*, *Actinobacillus actinomycetemcomitans*, *Bacillus* sp. (such as *Bacillus anthracis*, *Bacillus cereus*, *Bacillus subtilis*, *Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae*, *Bifidobacterium* sp., *Bordetella* sp. (such as *Bordetella pertussis*, *Bordetella parapertussis*, and *Bordetella bronchiseptica*), *Borrelia* sp. (such as *Borrelia recurrentis*, and *Borrelia burgdorferi*), *Brucella* sp. (such as *Brucella abortus*, *Brucella canis*, *Brucella melitensis* and *Brucella suis*), *Burkholderia* sp. (such as *Burkholderia pseudomallei* and *Burkholderia cepacia*), *Campylobacter* sp. (such as *Campylobacter jejuni*, *Campylobacter coli*, *Campylobacter lari* and *Campylobacter fetus*), *Capnocytophaga* sp., *Cardiobacterium hominis*, *Chlamydia trachomatis*, *Chlamydophila pneumoniae*, *Chlamydophila psittaci*, *Citrobacter* sp. *Coxiella burnetiid*, *Corynebacterium* sp. (such as, *Corynebacterium diphtheriae*, *Corynebacterium jeikeium* and *Corynebacterium*), *Clostridium* sp. (such as *Clostridium perfringens*, *Clostridium difficile*, *Clostridium botulinum* and *Clostridium tetani*), *Eikenella corrodens*, *Enterobacter* sp. (such as *Enterobacter aerogenes*, *Enterobacter agglomerans*, *Enterobacter cloacae*, and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chaffeensis* and *Ehrlichia canis*), *Epidermophyton floccosum*, *Erysipelothrix rhusiopathiae*, *Eubacterium* sp., *Francisella tularensis*, *Fusobacterium nucleatum*, *Gardnerella vaginalis*, *Gemella morbillorum*, *Haemophilus* sp. (such as *Haemophilus influenzae*, *Haemophilus ducreyi*, *Haemophilus aegyptius*, *Haemophilus parainfluenzae*, *Haemophilus haemolyticus* and *Haemophilus parahaemolyticus*, *Helicobacter* sp. (such as *Helicobacter pylori*, *Helicobacter cinaedi* and *Helicobacter fennelliae*), *Kingella kingae*, *Klebsiella* sp. (such as *Klebsiella pneumoniae*, *Klebsiella granulomatis* and *Klebsiella oxytoca*), *Lactobacillus* sp., *Listeria monocytogenes*, *Leptospira interrogans*, *Legionella pneumophila*, *Leptospira interrogans*, *Peptostreptococcus* sp., *Mannheimia haemolytica*, *Microsporum canis*, *Moraxella catarrhalis*, *Morganella* sp., *Mobiluncus* sp., *Micrococcus* sp., *Mycobacterium* sp. (such as *Mycobacterium leprae*, *Mycobacterium tuberculosis*, *Mycobacterium paratuberculosis*, *Mycobacterium intracellulare*, *Mycobacterium avium*, *Mycobacterium bovis*, and *Mycobacterium marinum*), *Mycoplasma* sp. (such as *Mycoplasma pneumoniae*, *Mycoplasma hominis*, and *Mycoplasma genitalium*), *Nocardia* sp. (such as *Nocardia asteroides*, *Nocardia cyriacigeorgica* and *Nocardia brasiliensis*), *Neisseria* sp. (such as *Neisseria gonorrhoeae* and *Neisseria meningitidis*), *Pasteurella multocida*, *Pityrosporum orbiculare* (*Malassezia furfur*), *Plesiomonas shigelloides*. *Prevotella* sp., *Porphyromonas* sp., *Prevotella melaninogenica*, *Proteus* sp. (such as *Proteus vulgaris* and *Proteus mirabilis*), *Providencia* sp. (such as *Providencia alcalifaciens*, *Providencia rettgeri* and *Providencia stuartii*), *Pseudomonas aeruginosa*, *Propionibacterium acnes*, *Rhodococcus equi*, *Rickettsia* sp. (such as *Rickettsia rickettsii*, *Rickettsia akari* and *Rickettsia prowazekii*, *Orientia tsutsugamushi* (formerly: *Rickettsia tsutsugamushi*) and *Rickettsia typhi*), *Rhodococcus* sp., *Serratia marcescens*, *Stenotrophomonas maltophilia*, *Salmonella* sp. (such as *Salmonella enterica*, *Salmonella typhi*, *Salmonella paratyphi*, *Salmonella enteritidis*, *Salmonella choleraesuis* and *Salmonella typhimurium*), *Serratia* sp. (such as *Serratia marcescens* and *Serratia liquefaciens*), *Shigella* sp. (such as *Shigella dysenteriae*, *Shigella flexneri*, *Shigella boydii* and *Shigella sonnei*), *Staphylococcus* sp. (such as *Staphylococcus aureus*, *Staphylococcus epidermidis*, *Staphylococcus haemolyticus*, *Staphylococcus agalactiae*, *Staphylococcus maltophilia*, *Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae*, *Streptococcus mutans*, *Streptococcus pyogenes*, Group A streptococci, *Streptococcus pyogenes*, Group B streptococci, *Streptococcus agalactiae*, Group C streptococci, *Streptococcus anginosus*, *Streptococcus equisimilis*, Group D streptococci, *Streptococcus bovis*, Group F streptococci, and *Streptococcus anginosus* Group G streptococci), *Spirillum minus*, *Streptobacillus moniliformis*, *Treponema* sp. (such as *Treponema carateum*, *Treponema pertenue*, *Treponema pallidum* and *Treponema endemicum*, *Trichophyton rubrum*, *T mentagrophytes*, *Tropheryma whippelii*, *Ureaplasma urealyticum*, *Veillonella* sp., *Vibrio* sp. (such as *Vibrio cholerae*, *Vibrio parahaemolyticus*, *Vibrio vulnificus*, *Vibrio parahaemolyticus*, *Vibrio vulnificus*, *Vibrio alginolyticus*, *Vibrio mimicus*, *Vibrio hollisae*, *Vibrio fluvialis*, *Vibrio metschnikovii*, *Vibrio damsela* and *Vibrio furnissii*), *Yersinia* sp. (such as *Yersinia enterocolitica*, *Yersinia pestis*, and *Yersinia pseudotuberculosis*) and *Xanthomonas maltophilia* among others.

Fungi

In any aspect or embodiment described herein, the infectious agent, pathogen, and/or microbe is a fungus or a fungal species. Examples of fungi that can be detected in accordance with the disclosed methods include without limitation any one or more of (or any combination of), *Aspergillus*, *Blastomyces*, Candidiasis, Coccidioidomycosis, *Cryptococcus neoformans*, *Cryptococcus gattii*, sp. *Histoplasma* sp. (such as *Histoplasma capsulatum*), *Pneumocystis* sp. (such as *Pneumocystis jirovecii*), *Stachybotrys* (such as *Stachybotrys chartarum*), Mucormycosis, *Sporothrix*, fungal eye infections ringworm, *Exserohilum*, *Cladosporium*.

In certain example embodiments, the fungus is a yeast. Examples of yeast that can be detected in accordance with disclosed methods include without limitation one or more of (or any combination of), *Aspergillus* species (such as *Aspergillus fumigatus*, *Aspergillus flavus* and *Aspergillus clavatus*), *Cryptococcus* sp. (such as *Cryptococcus neoformans*, *Cryptococcus gattii*, *Cryptococcus laurentii* and *Cryptococcus albidus*), a *Geotrichum* species, a *Saccharomyces* species, a *Hansenula* species, a *Candida* species (such as *Candida albicans*), a *Kluyveromyces* species, a *Debaryomyces* species, a *Pichia* species, or combination thereof. In certain example embodiments, the fungi is a mold. Example molds include, but are not limited to, a *Penicillium* species, a *Cladosporium* species, a *Byssochlamys* species, or a combination thereof.

Protozoa

In any aspect or embodiment described herein, the infectious agent, pathogen, and/or microbe is a protozoa. Examples of protozoa that can be detected in accordance with the disclosed methods include without limitation any one or more of (or any combination of), Euglenozoa, Heterolobosea, Diplomonadida, Amoebozoa, Blastocystis, and Apicomplexa. Example Euglenozoa include, but are not limited to, *Trypanosoma cruzi* (Chagas disease), *T. brucei gambiense*, *T. brucei rhodesiense*, *Leishmania braziliensis*, *L. infantum*, *L. mexicana*, *L. major*, *L. tropica*, and *L. donovani*. Example *Heterolobosea* include, but are not limited to, *Naegleria fowleri*. Example Diplomonadida include, but are not limited to, *Giardia intestinalis* (*G. lamblia*, *G. duodenalis*). Example Amoebozoa include, but are not limited to, *Acanthamoeba castellanii*, *Balamuthia mandrillaris*, *Entamoeba histolytica*. Example Blastocysts include, but are not limited to, *Blastocystis hominis*. Example Apicomplexa include, but are not limited to, *Babesia micron*, *Cryptosporidium parvum*, *Cyclospora cayetanensis*, *Plasmodium falciparum*, *P. vivax*, *P. ovale*, *P. malariae*, and *Toxoplasma gondii*.

Parasites

In any aspect or embodiment described herein, the infectious agent, pathogen, and/or microbe is a parasite. Examples of parasites that can be detected in accordance with disclosed methods include without limitation one or more of (or any combination of), an *Onchocerca* species and a *Plasmodium* species.

Malaria is a mosquito-borne pathology caused by *Plasmodium* parasites. The parasites are spread to people through the bites of infected female Anopheles mosquitoes. Five *Plasmodium* species cause malaria in humans: *Plasmodium falciparum*, *Plasmodium vivax*, *Plasmodium ovale*, *Plasmodium malariae*, and *Plasmodium knowlesi*., each of which can be detected in accordance with the disclosed methods.

Viruses

In any aspect or embodiment described herein, the infectious agent, pathogen, and/or microbe a virus, a viral infection (e.g., of a subject, including non-human animals and plants), a particular viral strain (including viral strains that differ by a single nucleotide polymorphism). The virus may be a DNA virus or an RNA virus, such as a retrovirus. Non-limiting example of viruses that can be detected with the disclosed methods include, but are not limited to, one or more of (or any combination of) Ebola, measles, SARS, Chikungunya, hepatitis, Marburg, yellow fever, MERS, Dengue, Lassa, influenza, rhabdovirus or HIV. A hepatitis virus may include hepatitis A, hepatitis B, or hepatitis C. An influenza virus may include, for example, influenza A or influenza B. An HIV may include HIV 1 or HIV 2. In certain example embodiments, the viral sequence may be a human respiratory syncytial virus, Sudan ebola virus, Bundibugyo virus, Tai Forest ebola virus, Reston ebola virus, Achimota, Aedes flavivirus, Aguacate virus, Akabane virus, Alethinophid reptarenavirus, Allpahuayo mammarenavirus, Amapari mammarenavirus, Andes virus, Apoi virus, Aravan virus, Aroa virus, Arumwot virus, Atlantic salmon paramyxovirus, Australian bat lyssavirus, Avian bornavirus, Avian metapneumovirus, Avian paramyxoviruses, penguin or Falkland Islandsvirus, BK polyomavirus, Bagaza virus, Banna virus, Bat herpesvirus, Bat sapovirus, Bear Canon mammarenavirus, Beilong virus, Betacoronavirus, Betapapillomavirus 1-6, Bhanja virus, Bokeloh bat lyssavirus, Borna disease virus, Bourbon virus, Bovine hepacivirus, Bovine parainfluenza virus 3, Bovine respiratory syncytial virus, Brazoran virus, Bunyamwera virus, Caliciviridae virus. California encephalitis virus, Candiru virus, Canine distemper virus, Canine pneumovirus, Cedar virus, Cell fusing agent virus, Cetacean morbillivirus, Chandipura virus, Chaoyang virus, Chapare mammarenavirus, Chikungunya virus, Colobus monkey papillomavirus, Colorado tick fever virus, Cowpox virus, Crimean-Congo hemorrhagic fever virus, Culex flavivirus, Cupixi mammarenavirus, Dengue virus, Dobrava-Belgrade virus, Donggang virus, Dugbe virus, Duvenhage virus, Eastern equine encephalitis virus, Entebbe bat virus, Enterovirus A-D, European bat lyssavirus 1-2, Eyach virus, Feline morbillivirus, Fer-de-Lance paramyxovirus, Fitzroy River virus, Flaviviridae virus, Flexal mammarenavirus, GB virus C, Gairo virus, Gemycircularvirus, Goose paramyxovirus SF02, Great Island virus, Guanarito mammarenavirus, Hantaan virus, Hantavirus Z10, Heartland virus, Hendra virus, Hepatitis A/B/C/E, Hepatitis delta virus, Human bocavirus, Human coronavirus, Human endogenous retrovirus K, Human enteric coronavirus, Human genital-associated circular DNA virus-1, Human herpesvirus 1-8, Human immunodeficiency virus 1/2, Human mastadenovirus A-G, Human papillomavirus, Human parainfluenza virus 1-4, Human parechovirus, Human picornavirus, Human smacovirus, Ikoma lyssavirus, Ilheus virus, Influenza A-C, Ippy mammarenavirus, Irkut virus, J-virus, JC polyomavirus, Japanese encephalitis virus, Junin mammarenavirus, KI polyomavirus, Kadipiro virus, Kamiti River virus, Kedougou virus, Khujand virus, Kokobera virus, Kyasanur forest disease virus, Lagos bat virus, Langat virus, Lassa mammarenavirus, Latino mammarenavirus, Leopards Hill virus, Liao ning virus, Ljungan virus, Lloviu virus, Louping ill virus, Lujo mammarenavirus, Luna mammarenavirus, Lunk virus, Lymphocytic choriomeningitis mammarenavirus, Lyssavirus Ozernoe, MSI512\.225 virus, Machupo mammarenavirus, Mamastrovirus 1, Manzanilla virus, Mapuera virus, Marburg virus, Mayaro virus, Measles virus, Menangle virus, Mercadeo virus, Merkel cell polyomavirus, Middle East respiratory syndrome coronavirus, Mobala mammarenavirus, Modoc virus, Mojiang virus, Mokola virus, Monkeypox virus, Montana myotis leukoencephalitis virus, Mopeia lassa virus reassortant 29, Mopeia mammarenavirus, Morogoro virus, Mossman virus, Mumps virus, Murine pneumonia virus, Murray Valley encephalitis virus, Nariva virus, Newcastle disease virus, Nipah virus, Norwalk virus, Norway rat hepacivirus, Ntaya virus, O'nyong-nyong virus, Oliveros mammarenavirus, Omsk hemorrhagic fever virus, Oropouche virus, Parainfluenza virus 5, Parana mammarenavirus, Parramatta River virus, Peste-des-petits-ruminants virus, Pichande mammarenavirus, Picornaviridae virus, Pirital mammarenavirus, Piscihepevirus A, Porcine parainfluenza virus 1, porcine rubulavirus, Powassan virus, Primate T-lymphotropic virus 1-2, Primate erythroparvovirus 1, Punta Toro virus, Puumala virus, Quang Binh virus, Rabies virus, Razdan virus, Reptile bornavirus 1, Rhinovirus A-B, Rift Valley fever virus, Rinderpest virus, Rio Bravo virus, Rodent Torque Teno virus, Rodent hepacivirus, Ross River virus, Rotavirus A-I, Royal Farm virus, Rubella virus, Sabia mammarenavirus, Salem virus, Sandfly fever Naples virus, Sandfly fever Sicilian virus, Sapporo virus, Sathuperi virus, Seal anellovirus, Semliki Forest virus, Sendai virus, Seoul virus, Sepik virus, Severe acute respiratory syndrome-related coronavirus, Severe fever with thrombocytopenia syndrome virus, Shamonda virus, Shimoni bat virus, Shuni virus, Simbu virus, Simian torque teno virus, Simian virus 40-41, Sin Nombre virus, Sindbis virus, Small anellovirus, Sosuga virus, Spanish goat encephalitis virus, Spondweni virus, St. Louis encephalitis virus, Sunshine virus, TTV-like mini virus, Tacaribe mammarenavirus, Taila virus, Tamana bat virus, Tamiami mammarenavirus, Tembusu virus, Thogoto virus, Thottapalayam virus, Tick-borne encephalitis virus, Tioman virus, Togaviridae virus, Torque teno canis virus, Torque teno douroucouli virus, Torque teno felis virus, Torque teno midi virus, Torque teno sus virus, Torque teno tamarin virus, Torque teno virus, Torque teno 116 alophus virus, Tuhoko virus, Tula virus, Tupaia paramyxovirus, Usutu virus, Uukuniemi virus, Vaccinia virus, Variola virus, Venezuelan equine encephalitis virus, Vesicular stomatitis Indiana virus, WU Polyomavirus, Wesselsbron virus, West Caucasian bat virus, West Nile virus, Western equine encephalitis virus, Whitewater Arroyo mammarenavirus, Yellow fever virus, Yokose virus, Yug Bogdanovac virus, Zaire ebolavirus, Zika virus, or Zygosaccharomyces bailii virus Z viral sequence. Examples of RNA viruses that may be detected include one or more of (or any combination of) Coronaviridae virus, a Picornaviridae virus, a Caliciviridae virus, a Flaviviridae virus, a Togaviridae virus, a Bornaviridae, a Filoviridae, a Paramyxoviridae, a Pneumoviridae, a Rhabdoviridae, an Arenaviridae, a Bunyaviridae, an Orthomyxoviridae, or a Deltavirus. In certain example embodiments, the virus is Coronavirus, SARS, Poliovirus, Rhinovirus, Hepatitis A, Norwalk virus, Yellow fever virus, West Nile virus, Hepatitis C virus, Dengue fever virus, Zika virus, Rubella virus, Ross River virus, Sindbis virus, Chikungunya virus, Borna disease virus, Ebola virus, Marburg virus, Measles virus, Mumps virus, Nipah virus, Hendra virus, Newcastle disease virus, Human respiratory syncytial virus, Rabies virus, Lassa virus, Hantavirus, Crimean-Congo hemorrhagic fever virus, Influenza, or Hepatitis D virus.

In any aspect or embodiment described herein, the virus may be a plant virus selected from the group comprising Tobacco mosaic virus (TMV), Tomato spotted wilt virus (TSWV), Cucumber mosaic virus (CMV), Potato virus Y (PVY), the RT virus Cauliflower mosaic virus (CaMV), Plum pox virus (PPV), Brome mosaic virus (BMV), Potato virus X (PVX), Citrus tristeza virus (CTV), Barley yellow dwarf virus (BYDV), Potato leafroll virus (PLRV), Tomato bushy stunt virus (TBSV), rice tungro spherical virus (RTSV), rice yellow mottle virus (RYMV), rice hoja blanca virus (RHBV), maize rayado fino virus (MRFV), maize dwarf mosaic virus (MDMV), sugarcane mosaic virus (SCMV), Sweet potato feathery mottle virus (SPFMV), sweet potato sunken vein closterovirus (SPSVV), Grapevine fanleaf virus (GFLV), Grapevine virus A (GVA), Grapevine virus B (GVB), Grapevine fleck virus (GFkV), Grapevine leafroll-associated virus-1, -2, and -3, (GLRaV-1, -2, and -3), Arabis mosaic virus (ArMV), or Rupestris stem pitting-associated virus (RSPaV). In any aspect or embodiment described herein, the target DNA molecule is part of said pathogen or transcribed from a DNA molecule of said pathogen. For example, the target DNA sequence may be comprised in the genome of an RNA virus.

In any aspect or embodiment described therein, the virus is a retrovirus. Example retroviruses that may be detected using the embodiments disclosed herein include one or more of (or any combination of) viruses of the Genus Alpharetrovirus, Betaretrovirus, Gammaretrovirus, Deltaretrovirus, Epsilonretrovirus, Lentivirus, Spumavirus, or the Family Metaviridae, Pseudoviridae, and Retroviridae (including HIV), Hepadnaviridae (including Hepatitis B virus), and Caulimoviridae (including Cauliflower mosaic virus)

In any aspect or embodiment described therein, the virus is a DNA virus. Example DNA viruses that may be detected using the embodiments disclosed herein include one or more of (or any combination of) viruses from the Family Myoviridae, Podoviridae, Siphoviridae, Alloherpesviridae, Herpesviridae (including human herpes virus, and Varicella Zoster virus), Malocoherpesviridae, Lipothrixviridae, Rudiviridae, Adenoviridae, Ampullaviridae, Ascoviridae, Asfarviridae (including African swine fever virus), Baculoviridae, Cicaudaviridae, Clavaviridae, Corticoviridae, Fuselloviridae, Globuloviridae, Guttaviridae, Hytrosaviridae, Iridoviridae, Marseilleviridae, Mimiviridae, Nudiviridae, Nimaviridae, Pandoraviridae, Papillomaviridae, Phycodnaviridae, Plasmaviridae, Polydnaviruses, Polyomaviridae (including Simian virus 40, JC virus, BK virus), Poxviridae (including Cowpox and smallpox), Sphaerolipoviridae, Tectiviridae, Turriviridae, Dinodnavirus, S alterprovirus, and Rhizidiovirus.

Amplification

In any aspect or embodiment described herein, the method further comprises, prior to incubating the sample with the detection mixture, amplifying the target DNA sequence in the sample, wherein the sample incubated with the detection mixture is the amplification product (also known as amplicons), or a portion thereof. In any aspect or embodiment described herein, the method further comprises, while incubating the sample with the detection mixture, amplifying the target DNA sequence in the sample, wherein the sample incubated with the detection mixture is the amplification product or amplicons, or a portion thereof.

In any aspect or embodiment described herein, the method further comprises, prior to incubating the sample with the detection mixture, performing a reaction to amplify the target DNA sequence in the sample, wherein the sample incubated with the detection mixture is the amplification product or amplicons, or a portion thereof. In any aspect or embodiment described herein, the method further comprises, while incubating the sample with the detection mixture, performing a reaction to amplify the target DNA sequence in the sample, wherein the sample incubated with the detection mixture is the amplification product or amplicons, or a portion thereof.

In any aspect or embodiment described herein, the method further comprises, prior to incubating the sample with the detection mixture, performing a recombinase polymerase amplification (RPA) reaction to amplify the target DNA sequence in the sample, wherein the sample incubated with the detection mixture is the amplification product or amplicons, or a portion thereof. In any aspect or embodiment described herein, the method further comprises, while incubating the sample with the detection mixture, performing a recombinase polymerase amplification (RPA) reaction to amplify the target DNA sequence in the sample, wherein the sample incubated with the detection mixture is the amplification product or amplicons, or a portion thereof.

In any aspect or embodiment described herein, the method further comprises performing a RPA reaction to amplify the target DNA sequence.

In any aspect or embodiment described herein, when the method includes amplifying the target DNA sequence in the sample, the detection mixture may further comprise reagents for a RPA reaction (for example, one or more of a forward primer and reverse primer specific for dsDNA that includes the target DNA sequence, nucleotides (i.e., deoxynucleoside triphosphate (dNTP); such as, one or more of deoxyadenosine triphosphate (dATP), deoxythymidine triphosphate (dTTP), deoxycytidine triphsphate (dCTP), or deoxyguanosine triphosphate (dGTP)) required for amplification for use in reserves transcription and/or amplification, a crowding agent such as a high molecular polyethylene glycol, one or more strand-displacing polymerase (such as large fragment of *Bacillus subtilis* Pol 1, Bsu), one or more reverse transcriptases, one or more recombinases, one or more single-stranded DNA-binding proteins (SSB), adenosine triphosphate (ATP)).

In any aspect or embodiment described herein, when the method includes amplifying the target DNA sequence in the sample, the ssDNA sequence of the gRNA that hybridizes with (or that is complementary to) a sequence of the target DNA sequence is about 10 base pairs to about 30 base pairs long (for example, about 15 to about 25 base pairs or about 20 base pairs long).

In any aspect or embodiment described herein, when the method includes amplifying the target DNA sequence in the sample, the nucleic acid sequence of the nucleic acid probe that hybridizes with or that is complementary to a nucleic acid sequence of the target DNA sequence is about 4 base pairs to about 20 base pairs long. For example, in any aspect or embodiment described herein, when the method includes amplifying the target DNA sequence in the sample, the nucleic acid sequence of the nucleic acid probe that hybridizes with or that is complementary to a nucleic acid sequence of the target DNA sequence is about 4 to about 15 base pairs or about 4 to about 10 base pairs long.

In any aspect or embodiment described herein, when the method includes amplifying the target DNA sequence in the sample, incubating the amplification product or amplicons, or a portion thereof, is performed at about 35° C. to about 40° C. (e.g., about 37° C.). For example, in any aspect or embodiment described herein, when the method includes amplifying the target DNA sequence in the sample, incubating the amplification product or amplicons, or a portion thereof, is performed at a temperature that denatures double-stranded DNA (dsDNA) and/or at a temperature that separates the two strands of dsDNA that includes the target DNA sequence.

In any aspect or embodiment described herein, when the method includes performing a RPA reaction, the RPA reaction is performed at about 35° C. to about 42° C. For example, in any aspect or embodiment described herein, when the method includes performing a RPA reaction, the RPA reaction is performed at about 35° C. to about 40° C. or about 37° C.

In any aspect or embodiment described herein, when the method includes amplifying the target DNA sequence in the sample, the gRNA is about 35 to about 50 base pairs long. For example, in any aspect or embodiment described herein, when the method includes amplifying the target DNA sequence in the sample, the gRNA is about 35 to about 45 base pairs or about 40 to about 45 base pairs long.

In any aspect or embodiment described herein, when the method includes amplifying the target DNA sequence in the sample, amplifying is an isothermal amplification. In any aspect or embodiment described herein, when the method includes performing a RPA reaction, the RPA reaction is an isothermal amplification. Isothermal amplification utilizes a single temperature to amplify RNA or DNA targets eliminating the need for thermal cycling required in a polymerase chain reaction (PCR) amplification.

In any aspect or embodiment described herein, when the method includes amplifying the target DNA sequence in the sample, amplifying is performed for about 10 minutes to about 60 minutes. For example, in any aspect or embodiment described herein, when the method includes amplifying the target DNA sequence in the sample, amplifying is performed for about 30 minutes to about 60 minutes, about 35 minutes to about 50 minutes, or about 40 minutes.

In any aspect or embodiment described herein, when the method includes amplifying the target DNA sequence in the sample, the method is performed in a reaction chamber of an electrochemical sensor.

In any aspect or embodiment described herein, when the method includes amplifying the target DNA sequence in the sample, the method is performed in a solution phase (e.g., a single solution phase).

In any aspect or embodiment described herein, when the method includes amplifying the target DNA sequence in the sample, the method is performed in a homogeneous solution.

In any aspect or embodiment described herein, the RPA reagents can include optionally one or more reverse transcriptases, one or more recombinases, one or more single-stranded DNA-binding proteins (SSB), and one or more strand-displacing polymerase (such as, large fragment of *Bacillus subtilis* Pol 1, Bsu), ATP, a crowding agent such as a high molecular polyethylene glycol, deoxynucleotides (dNTPs) for use in reverse transcription (optional) and amplification, and forward and reverse primers specific for one or more of the target nucleic acids to be detected.

In any aspect or embodiment described herein, the DNA sequence is a cDNA that can be produced prior to incubating and/or amplification (for example, RPA) or in the same reaction. By including reverse transcriptase in an amplification reaction, the separate step of cDNA preparation is not required. Reverse transcriptases are known in the art, including Transcriptor® (Roche), Sensiscript® (Qiagen), or MuLV® (Applied Biosystems), to name a few. In any aspect or embodiment described herein, the concentration of a reverse transcriptase is in a range of from about 0.01 mg/mL to about 0.05 g/mL, about 0.01 mg/mL to about 0.1 mg/mL, about 0.01 mg/mL to about 0.15 mg/mL, about 0.05 mg/mL to about 0.1 mg/mL, about 0.05 mg/mL to about 0.15 mg/mL, or about 0.10 mg/mL to about 0.15 mg/mL.

In any aspect or embodiment described herein, the RPA reagents include a recombinase (for example, T4 UvsX or T4 UvsY from T4-like bacteriophages). The recombinase can form complexes with oligonucleotide primers and pair the primers with their homologous sequences in duplex DNA. In any aspect or embodiment described herein, the concentration of a recombinase is in a range of from about 0.01 mg/mL to about 0.05 mg/mL, about 0.01 mg/mL to about 0.1 mg/mL, about 0.01 mg/mL to about 0.15 mg/mL, about 0.05 mg/mL to about 0.1 mg/mL, about 0.05 mg/mL to about 0.15 mg/mL, or about 0.10 mg/mL to about 0.15 mg/mL.

In any aspect or embodiment described herein, the RPA reagents comprise one or more single-stranded DNA binding (SSB) proteins. A non-limiting example of a suitable SSB protein is T4 gp32 protein. SSB protein binds to the displaced DNA strand and stabilizes the resulting D loop. In any aspect or embodiment herein, the concentration of the SSB protein is about 0.1 mg/mL to about 0.5 mg/mL or about 0.6 mg/mL to about 1.0 mg/mL.

In any aspect or embodiment described herein, the RPA reagents comprise an isothermal DNA polymerase. Instead of melting DNA strands apart at high temperature, isothermal amplification takes advantage of DNA polymerases with high strand displacement activity that can directly unzip/separate the DNA and synthesize complementary strands. The reaction can occur at temperatures from 22° C. to 45° C. and can be optimized at temperatures between 37° C. and 42° C. Such DNA polymerases are known in the art, for example Sau, Bst or Phi29 DNA polymerases, to name a few. In any aspect or embodiment described herein, the concentration of the DNA polymerase is about 0.01 mg/mL to about 0.05 mg/mL or about 0.06 mg/mL to about 0.1 mg/mL.

In any aspect or embodiment described herein, the amplification or RPA reagents include dNTPs used at any concentration appropriate for the reaction, such as including, but not limited to, a concentration of about 100 nM to about 500 nM, 600 nM to about 1 mM, about 2 mM to about 10 mM, about 20 mM to about 100 mM, 200 mM to about 500 mM, or the like.

In any aspect or embodiment described herein, the RPA reagents comprise one or more additional components. Non-limiting examples of suitable addotopma; components include DL-Dithiothreitol, phosphocreatine disodium hydrate, creatine kinase, and adenosine 5'-triphosphate disodium salt.

In any aspect or embodiment described herein, the amplification or RPA reagents include a forward nucleic acid primer and a reverse nucleic acid primer, each used as any concentration appropriate for the reaction. Design of primers for amplification and reverse transcription is known in the art and involves choice of target region, design of primer candidates, and routine experimental screening. For example, designed primers of about 30-35 based in length can be used for RPA. Optimization of primer concentrations as primers compete for the recombinase proteins and ratios of each may be tested experimentally. Such testing is routine in the art. In any aspect or embodiment described herein, the primers may be designed by alignment and identification of conserved sequences in a target pathogen (e.g., using Clustal X or a similar program) and then using a software program (e.g., PrimerExplorer). The specificity of different candidate primers and gRNA or crRNA may be confirmed using a Basic Local Alignment Search Tool (BLAST) search of the GenBank nucleotide database. Primers may be synthesized using any method known in the art. For example, in any aspect or embodiment described herein, primers may be synthesized by chemical synthesis, genetic engineering techniques, and/or artificial manipulation of isolated segments of nucleic acids.

Examples of primers for HPV-16 L1 gene are shown in Table 1. In any aspect or embodiment described herein, at least one RPA forward primer or RPA reverse primer is at least 1 base pair, at least 2 base pairs, at least 3 base pairs, at least 4 base pairs, or at least 5 base pairs longer or shorter than the primers in Table 1. In any aspect or embodiment described herein, the concentration of each of the forward primer and reverse primer is individually at least 0.2 µM, at least 0.3 µM, at least 0.4 µM, at least 0.5 µM, up to 100 nM or 500 nM. In any aspect or embodiment described herein, the concentration of each of the forward primer and the reserves primes is individually in a range from about 0.2 µM to about 0.6 µM or about 0.3 µM to about 0.6 µM.

Specificity and Sensitivity

In any aspect or embodiment described herein, the methods described herein detects a target DNA sequence in a sample having a relatively low concentration of the target DNA sequence (e.g., the method, as well as test and systems implementing the same, has a relatively low limit of detection for the target DNA sequence). In any aspect or embodiment described herein, the method described herein detects a target DNA sequence at a concentration of at least 5 genomic copies per µL, at least 6 genomic copies per µL, at least 7 genomic copies per µL, at least 8 genomic copies per µL, at least 9 genomic copies per µL, at least 10 genomic copies per µL, at least 15 genomic copies per µL, or at least 20 genomic copies per µL. In any aspect or embodiment described herein, the method described herein detects a target DNA sequence at a concentration in a range from 5-6 genomic copies per µL, 5-7 genomic copies per µL, 5-8 genomic copies per µL, 5-9 genomic copies per µL, 5-10 genomic copies per µL, 5-15 genomic copies per µL, 5-20 genomic copies per µL, 8-10 genomic copies per µL, 8-15 genomic copies per µL, 8-20 genomic copies per µL, 10-15 genomic copies per µL, or 10-20 genomic copies per µL. In any aspect or embodiment described herein, the method described herein detects 1000 copies or more, 900 or more copies, 800 or more copies, 700 or more copies, 600 or more copies, 500 or more copies, 450 or more copies, 400 or more copies, 350 or more copies, 300 or more copies, 250 or more copies, 200 or more copies, 150 or more copies, 100 or more copies, 50 or more copies, or 25 or more copies of the target DNA sequence.

In any aspect or embodiment described herein, the method detects 200 or more copies of the target DNA sequence (or 200 or more genome equivalents (GE) per reaction).

In any aspect or embodiment described herein, when the method includes amplifying the target DNA sequence in the sample, the method detects 100 or more copies of the target DNA sequence (or 100 or more GE per reaction).

Biosensor

The present disclosure further describes biosensors comprising an electrochemical sensor (e.g., electrochemical biosensor platform/device/apparatus) comprising the detection mixture.

In any aspect or embodiment described herein, the electrochemical sensor comprises a working electrode, a reference electrode, and/or an auxiliary electrode.

In any aspect or embodiment described herein, the biosensor comprises one or more of a multipurpose interface, a batch add-on coupled to the multipurpose interface, and an electrochemical sensor disposed on the multipurpose interface.

Kits

Any of the methods described herein may be formulated as a kit. As used herein a "kit" comprises a package or an assembly including one or more compositions and one or more apparatuses to implement the methods described herein. Any one of the kits provided herein may comprise any number of reaction tubes, wells, chambers, or other vessels. Each of the components of the kit (e.g., reagents) may be provided in liquid form (e.g., in solution). In any aspect or embodiment, one or more reagents described herein (e.g., lysis reagents, nucleic acid amplification reagents, reagents for CRISPR/Cas detection) are in solid form (e.g., lyophilized, dried, crystallized, air jetted). In any aspect or embodiment described herein, one or more (and, in some cases, all) nucleic acid amplification reagents are in solid form. In any aspect or embodiment described herein, one or more CRISPR/Cas detection reagents are in solid form. In any aspect or embodiment described herein, one or more (and, in some cases, all) lysis reagents are in solid form. In any aspect or embodiment described herein, all reagents of a diagnostic test or system that implement the method described herein are in solid form. In any aspect or embodiment described herein, the one or more reagents in solid form are in the form of one or more beads, pellets, and/or tablets. The one or more beads, pellets, and/or tablets may comprise any reagent or combination of reagents described herein. Therefore, some embodiments that do not require a supporting device are also contemplated, i.e., the system may be applied to any surface or fluid that will support the reactions disclosed herein and allow for detection of a positive detectable signal from that surface or solution. In addition to freeze-drying, the systems may also be stably stored and utilized in a pelletized form. Polymers useful in forming suitable pelletized forms are known in the art. In any aspect or embodiment described herein, the one or more beads, pellets, and/or tablets are stable at room temperature for a relatively long period of time. In any aspect or embodiment described herein, the one or more beads and/or tablets are stable at room temperature for about 1 month to about 6 months, about 9 months to about 2 years, or more.

A kit may, in any aspect or embodiment described herein, include instructions in any form that are provided in connection with the compositions for performing the methods described herein in such a manner that one of ordinary skill in the art would recognize that the instructions are to be associated with the compositions for performing the methods described herein. The instructions may include instructions for performing any one of the methods described herein. The instructions may include instructions for the use, modification, mixing, diluting, preserving, administering, assembly, storage, packaging, and/or preparation of the compositions and/or other compositions associated with the kit. The instructions may be provided in any form recognizable by one of ordinary skill in the art as a suitable vehicle for containing such instructions, for example, written or published, verbal, audible (e.g., telephonic), digital, optical, visual, or electronic communications (including Internet or web-based communications). In any aspect or embodiment described herein, the instructions are provided as part of a software-based application, as described herein. In any aspect or embodiment described herein, the kit contains a sterile swab.

In any aspect or embodiment described herein, the reagents (for example, the detection mixture, which may include the amplifying reagents and/or reverse transcription reagents, the amplifying reagents, reverse transcription reagents etc.) can be lyophilized and provided as such in a reaction chamber (for example, an electrochemical sensor) or in the form of a pellet to be added to a reaction chamber (for example, an electrochemical sensor). Lyophilized reagents are stable at ambient temperature for at least 6 months. In any aspect or embodiment described herein, each component of the methods, and diagnostic test and system implementing the same, is shelf stable for a relatively long period of time, and may be stored at room temperature (e.g., 20-25° C.) for at least 1 month, at least 3 months, at least 6 months, at least 9 months, at least 1 year, at least 5 years, at least 10 years.

Furthermore, in any aspect or embodiment described herein, one or more reagents of the methods described herein comprise one or more additives that may enhance reagent stability (e.g., protein stability and/or nucleic acid stability). Non-limiting examples of suitable additives include trehalose, polyethylene glycol (PEG), polyvinyl alcohol (PVA), and glycerol.

As shown in the Examples below, the methods described herein provides a rapid test for the detection of a nucleic acid sequence, such as for diagnostic purposes, which produces results in less than 2 hours with high sensitivity, allowing detection of 100 genome copies of the target nucleic acid sequence per test, with a specificity of 100%. In any aspect or embodiment described herein, the methods have a relatively high positive percent agreement (PPA) and/or a relatively high negative percent agreement (NPA) with a reference test. In some cases, the diagnostic system may be compared to a reference test by testing a certain number of subjects using both the diagnostic system and the reference test, and positive percent agreement and/or negative percent agreement values may be obtained. Positive percent agreement can be calculated by dividing the number of positive results obtained by the diagnostic system by the number of positive results obtained using the reference test and multiplying by 100. In some embodiments, the methods have a positive percent agreement with a reference test of at least 90%, at least 91%, at least 92%, at least 93%, at least 94%, at least 95%, at least 96%, at least 97%, at least 98%, at least 99%, or about 100%. In some embodiments, the methods have a positive percent agreement with a reference test in a range from 90-95%, 90-98%, 90-99%, 90-100%, 95-98%, 95-99%, 95-100%, 98-100%, or 99-100%. Negative percent agreement can be calculated by dividing the number of negative results obtained by the diagnostic system by the number of negative results obtained by the reference test and multiplying by 100. In some embodiments, the methods have a negative percent agreement with a reference test of at least 90%, at least 91%, at least 92%, at least 93%, at least 94%, at least 95%, at least 96%, at least 97%, at least 98%, at least 99%, or about 100%. In some embodiments, the methods have a negative percent agreement with a reference test in a range from 90-95%, 90-98%, 90-99%, 90-100%, 95-98%, 95-99%, 95-100%, 98-100%, or 99-100%.

In any aspect or embodiment described herein, the total time for performing the methods described herein is about 100 minutes or less, about 90 minutes or less, about 80 minutes or less, about 75 minutes or less, about 70 minutes or less, about 65 minutes or less, about 60 minutes or less, about 50 minutes or less, 45 minutes or less, about 40 minutes or less, or about 30 minutes or less. In any aspect or embodiment described herein, the total time for performing the methods described herein is in a range of about 30 to about 40 minutes, about 30 to about 45 minutes, about 30 to about 50 minutes, about 30 to about 60 minutes, about 30 to about 65 minutes, about 30 to about 70 minutes, about 30 to about 75 minutes, about 30 to about 80 minutes, about 30 to about 90 minutes, about 30 to about 100 minutes, about 45 to about 60 minutes, about 45 to about 65 minutes, about 45 to about 70 minutes, about 45 to about 75 minutes, about 45 to about 80 minutes, about 45 to about 90 minutes, about 45 to about 100 minutes, about 60 to about 70 minutes, about 60 to about 75 minutes, about 60 to about 80 minutes, about 60 to about 90 minutes, about 60 to about 100 minutes, about 70 to about 75 minutes, about 70 to about 80 minutes, about 70 to about 90 minutes, about 70 to about 100 minutes, about 75 to about 80 minutes, about 75 to about 90 minutes, about 75 to about 100 minutes, about 80 to about 90 minutes, or about 80 to about 100 minutes.

Reagents and Samples

CRISPR-based detection of HPV-16 DNA was carried out according to previous work. Briefly, the final CRISPR reaction system contained 200 nM LbCas12a, 250 nM crRNA, 1× buffer (50 mM NaCl, 10 mM Tris-HCl, 10 mM $MgCl_2$, 100 μg/ml BSA, pH 7.9 at 25° C.), 1 μM single-stranded methylene blue (ssDNA-MB), and DNA target. During on-chip CRISPR-based detection, pulsed electric fields (were generated by Trueform Series Waveform Generators 33520B (Keysight Technologies, CA, USA). The pulsed electric field was applied to the electrochemical CRISPR biosensor, where the working electrode served as a positive electrode and the reference/counter electrodes served as ground electrodes. Electrochemical signal detections can be performed on a CHI660D potentiostat (CH Instruments, TX, USA). Differential pulse voltammetry (DPV) can be applied to determine the redox peak current.

Optional, pre-amplification of HPV-16 DNA extracts by RPA amplification at 37° C. The 25 μL RPA reaction solution contained 1× reaction buffer, 1× basic E-mix, 1× core reaction buffer, 14 mM MgOAc, 0.32 μM each of forward and reverse primers, 0.8 mM of each nucleotide (dATP, dTTP, dCTP, dGTP), and 2 μL DNA extracts. After RPA amplification, 2 μL (or more of the) amplicons can be used for electrochemical CRISPR detection on the electrochemical CRISPR biosensor.

EXAMPLES

DNA detection plays an important role in the rapid screening of cancers and early diagnosis of infectious diseases. The present disclosure describes a simple, sensitive, versatile, immobilization-free, electric field-enhanced (EFE), electrochemical CRISPR biosensor to detect DNA in a homogeneous solution phase. To improve the detection sensitivity, a pulsed electric field was used to enrich nucleic acids on the working electrode surface. Various electrokinetic methods have been widely adapted to facilitate the concentration, transport, hybridization, and denaturation of DNA molecules. For instance, a high-frequency electric field has been used to concentrate DNA and minimize irreversible electrochemical reactions at the electrode surface. Some have proposed an electric field-assisted DNA immobilization approach to increase the DNA hybridization reaction rates. By using an electric field, some have demonstrated that DNA immobilization and hybridization rates were $10^9$ times faster compared with passive control reactions without electric fields. In addition, electrochemical DNA detection is compatible with electric field application on the electrode surface. Thus, electric fields can enrich nucleic acids and improve the detection sensitivity of electrochemical DNA biosensors.

Unlike previously reported electrochemical CRISPR biosensors with immobilized electroactive probes, the biosensor described herein employs an electroactive probe, e.g., a methylene blue (MB)-labeled ssDNA (ssDNA-MB), as the electrochemical signaling probe in a solution, specifically a homogeneous solution, eliminating the need for time-consuming immobilization procedures, which can also cause reduced cleavage efficiency and selectivity on the heterogeneous surface. By taking advantage of the trans-cleavage activity of CRISPR-Cas12a, the negatively charged ssDNA-MB probes are cleaved, thereby releasing the less negative MB-labeled probes, which can diffuse freely to the negatively charged working electrode and increase the electrochemical signal. To demonstrate the clinical utility of the EFE electrochemical CRISPR biosensor of the present disclosure, the biosensor may be coupled with recombinase polymerase amplification (RPA) to successfully detect HPV-16 DNA in clinical swab samples.

The simple, versatile, EFE, electrochemical CRISPR biosensor of the present disclosure are able to detect DNA targets in a solution phase. The sensitivity was improved through the application of a pulsed electric field that enriched nucleic acids on the electrode surface. The working principle of the EFE, immobilization-free, electrochemical CRISPR biosensor is schematically illustrated in FIG. 1. The EFE electrochemical CRISPR biosensor of the present disclosure takes advantage of the diffusivity difference between electrochemical oligonucleotide probes and CRISPR-cleaved probes toward a negatively charged working electrode, enabling simple and sensitive electrochemical detection of DNA without the need for complicated immobilization processing of electrochemical probes. The CRISPR biosensor of the present disclosure was able to directly detect unamplified human papillomavirus-16 (HPV-16) DNA with a sensitivity of 1 pM. Further, the EFE electrochemical CRISPR biosensor coupled with recombinase polymerase amplification (RPA) successfully detected HPV-16 DNA in clinical samples. Thus, the EFE electrochemical CRISPR biosensor of the present disclosure provides a simple, robust, and sensitive detection method for nucleic acid-based molecular diagnostics.

Materials and Methods

Reagents and Materials. All of the oligonucleotides (shown below in Table 1), crRNAs, and HPV-16 plasmid DNA were synthesized or purchased from Integrated DNA Technologies (IA, USA). LbCas12a, 10× NEBuffer™ 2.1 and nuclease-free water were purchased from New England BioLabs® (MA, USA). The TwistAmp® Liquid Basic Kit was purchased from TwistDx™ Ltd. (Maidenhead, UK) and the DNeasy® Blood & Tissue Kit was purchased from QIAGEN® (Hilden, Germany). The electrochemical sensor and its detection platform were obtained from MicruX™ Technologies (Asturias, Spain). All other chemicals used were of analytical reagent grade.

TABLE 1

Oligonucleotide Sequences of the Examples

| Oligonucleotide | Sequence |
| --- | --- |
| crRNA | |
| LbCas12a-crRNA-HPV-16 | UAAUUUCUACUAAGUGUAGAUUGAAGUAGAUAUGG CAGCAC (SEQ ID NO: 1) |
| Target | |
| HPV-16 L1 | ATAATGGCATTTGTTGGGGTAACCAACTATTTGTTACT GTTGTTGATACTACACGCAGTACAAATATGTCATTATG TGCTGCCATATCTACTTCAGAAACTACATATAAAATA CTAACTTTAAGGAGTACCTACGACATGGGGAGGAATA TGATTT (SEQ ID NO: 2) |
| RPA Primers | |
| FP_HPV16L1 | TTGTTGGGGTAACCAACTATTTGTTACTGTT (SEQ ID NO: 3) |
| RP_HPV16L1 | CCTCCCCATGTCTGAGGTACTCCTTAAAG (SEQ ID NO: 4) |
| Reporter | |
| ssDNA-FQ | /56-FAM/TTATT/3IABkFQ/ |
| ssDNA-MB | TTA TT/3MeB1N/ |

Crispr-Based Fluorescence Detection. CRISPR-based fluorescence detection of HPV-16 DNA was carried out according to previous work. Briefly, the final CRISPR reaction system contained 200 nM LbCas12a, 250 nM crRNA, 1× buffer (50 mM NaCl, 10 mM Tris-HCl, 10 mM MgCl$_2$, 100 µg/ml BSA, pH 7.9 at 25° C.), 1 µM single-stranded DNA fluorophore-quencher (ssDNA-FQ), and DNA target. The single-stranded DNA fluorophore-quencher probe has a fluorescein (6-FAM) on the 5' end of the single-stranded DNA sequence and a Iowa Black FQ on the 3'end of the single-stranded DNA sequence.

In-tube CRISPR Detection. The CRISPR reaction tubes were incubated at 37° C. for 60 minutes and the fluorescence signals were monitored in real time using the Bio-Rad CFX96 Touch™ Real-Time PCR Detection System (BIO-RAD® Laboratories, CA).

On-chip CRISPR Detection. The CRISPR reaction occurred in the chamber of the electrochemical detection platform (MicruX™ Technologies, Asturias, Spain), which includes a multipurpose interface, batch add-on, and electrochemical sensor. A digital block heater (VWR® Mini Block Heater, PA, USA) was used to incubate the electrochemical detection platform at 37° C. Mineral oil was added to the reaction chamber to minimize liquid evaporation during incubation. For fluorescence detection, a portable USB fluorescence microscope (AM4113T-GFBW, Dino-Lite® Premier, AnMo Electronics, Taiwan, China) was used to record the fluorescence signals of the electrochemical chamber in real time. Further, the fluorescence signals of the CRISPR reaction chamber were integrated and generated normalized average fluorescence intensities at every specified time interval (e.g., 1 minute interval for 60 minutes). Normalized fluorescence intensities were plotted against time to obtain real-time fluorescence curves of CRISPR detection.

Figure 2:
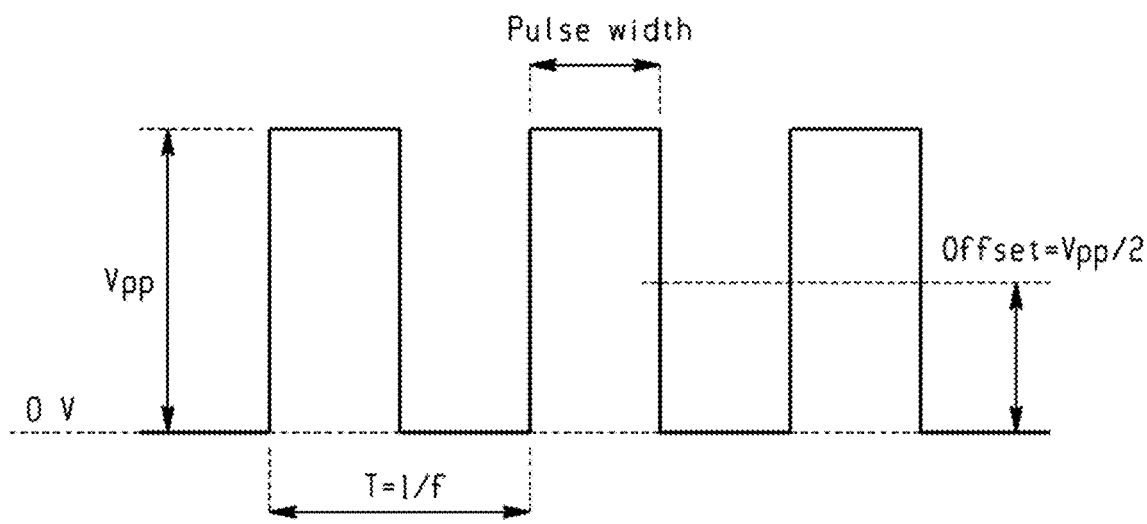
FIG. 2. Electric field waveform. Electric field consists of an AC electric field and a DC offset. The peak-to-peak potential (Vpp) is the amplitude of the electric field or electric potential of the AC electric field. In this embodiment, for purposes of illustration, the offset potential (i.e., the electric potential of the DC offset) is half of the Vpp and the pulse width is 50% of the period of the electric field (T) (i.e., the AC electric field and the DC offset). Those skilled in the art will appreciate that the Vpp, offset potential, and pulse width will vary based on the sequences to be detected and/or utilized in the detection process and that such optimization is routine in the art.
Figure 3A:
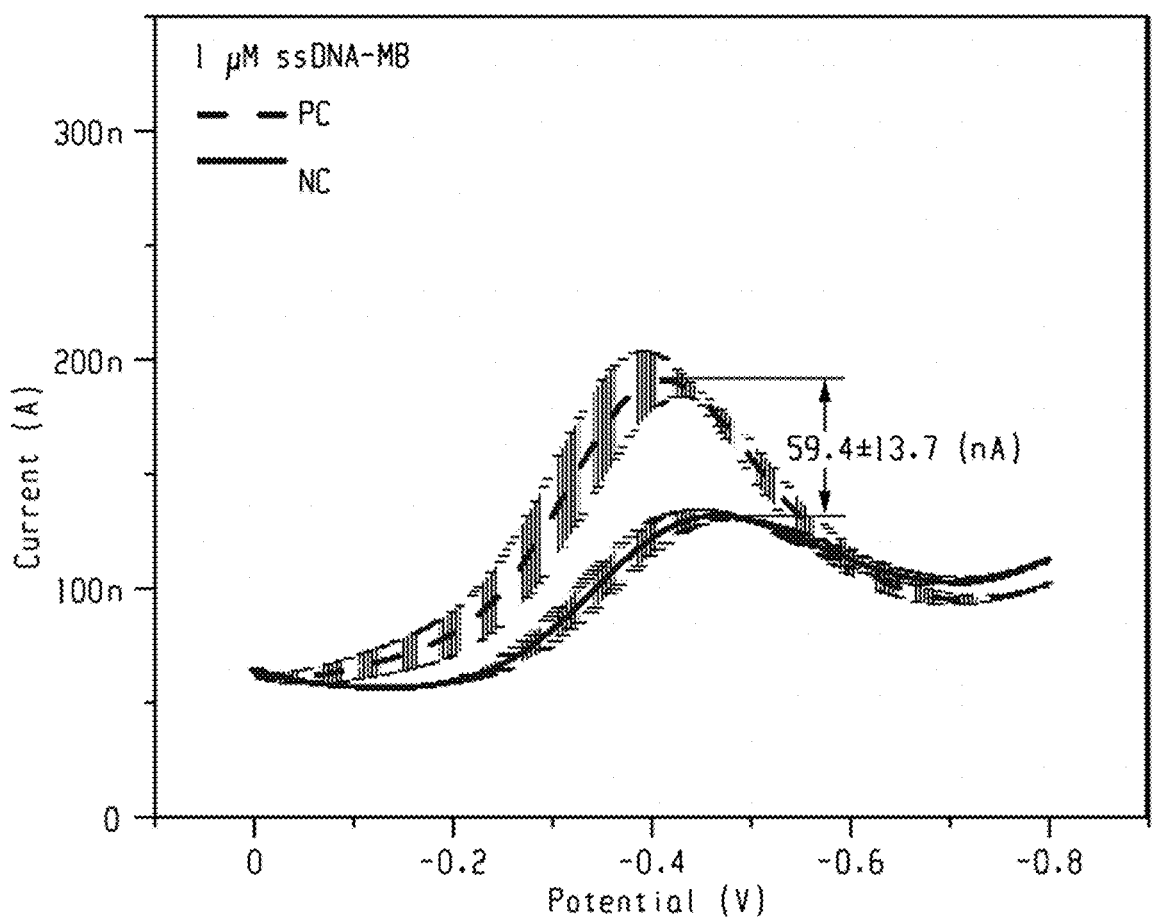
FIGS. 3A, 3B, 3C, 3D, and 3E. Optimization of the ssDNA-MB probe concentration for the EFE electrochemical CRISPR biosensor.
Figure 3B:
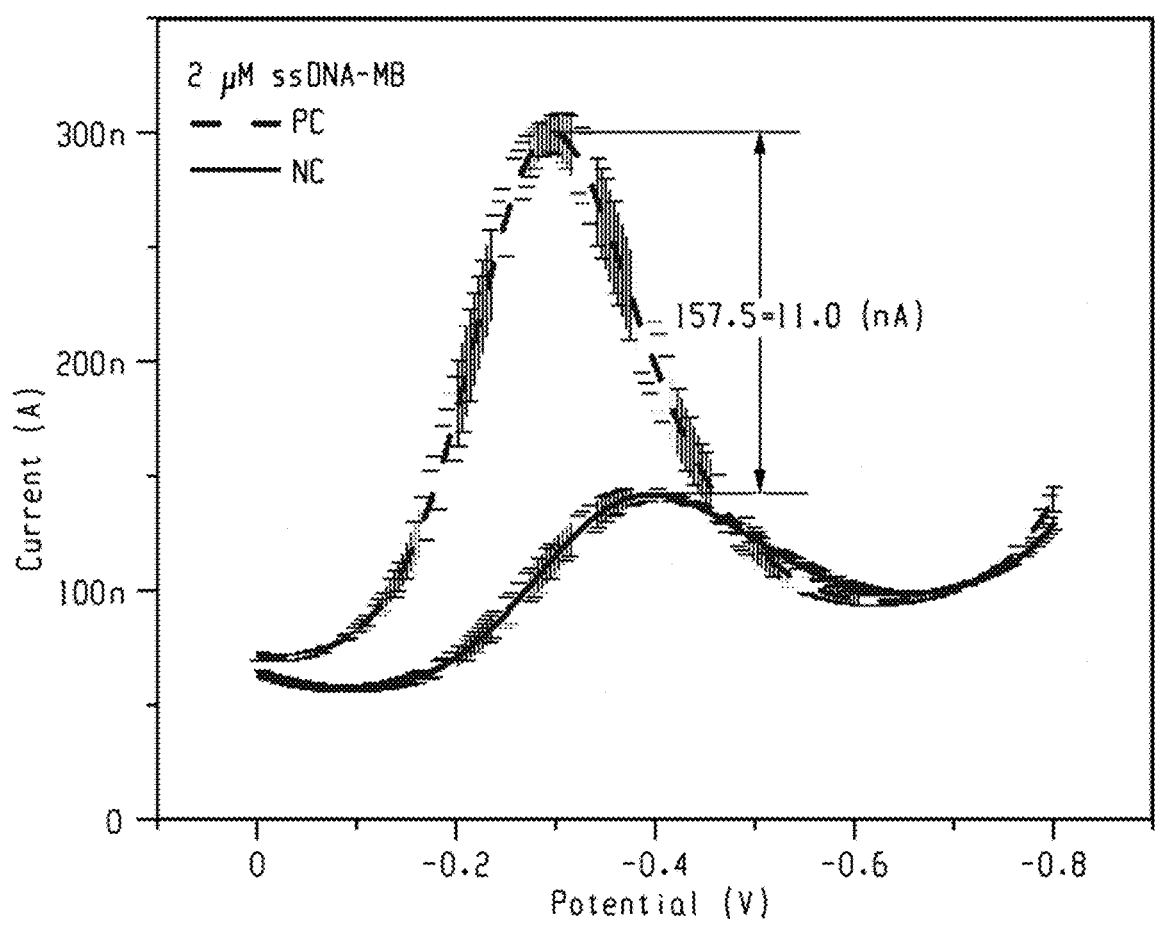
Figure 3C:
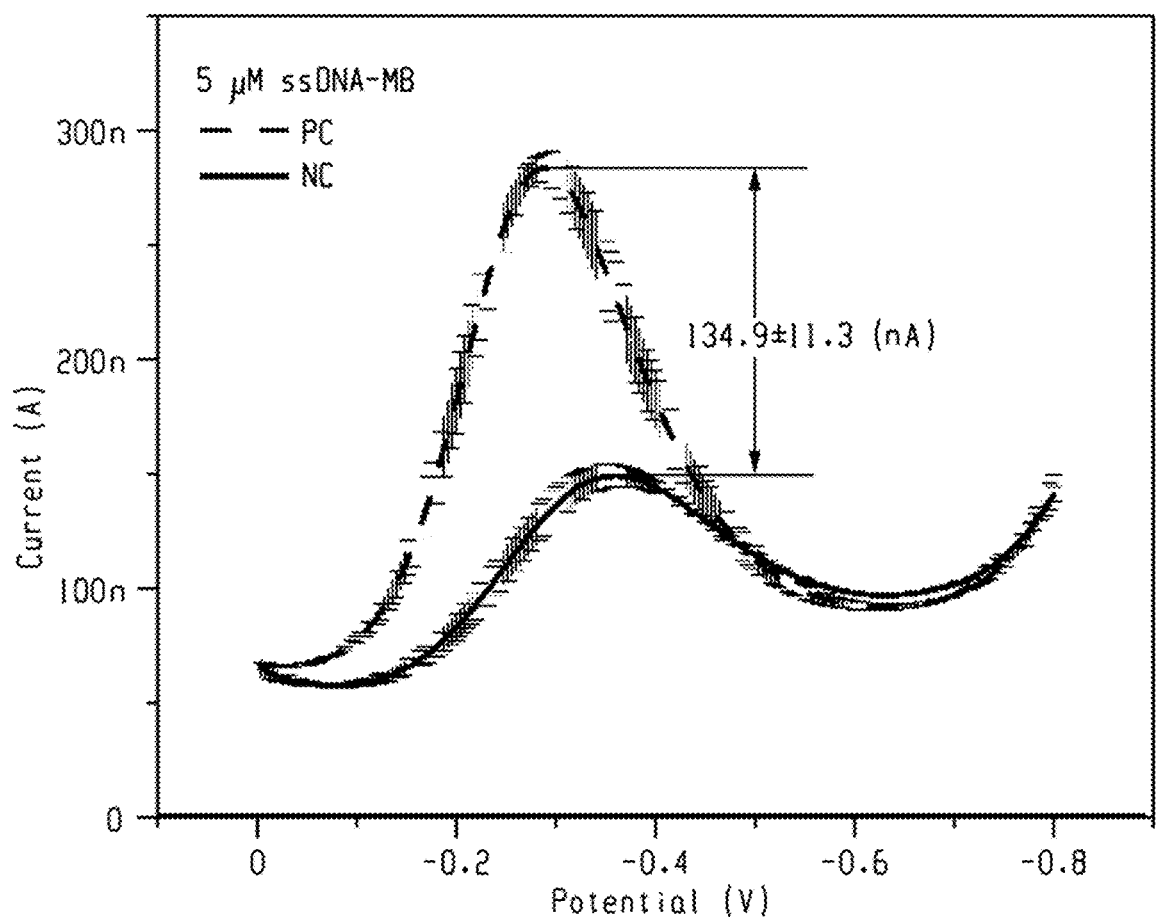
Figure 3D:
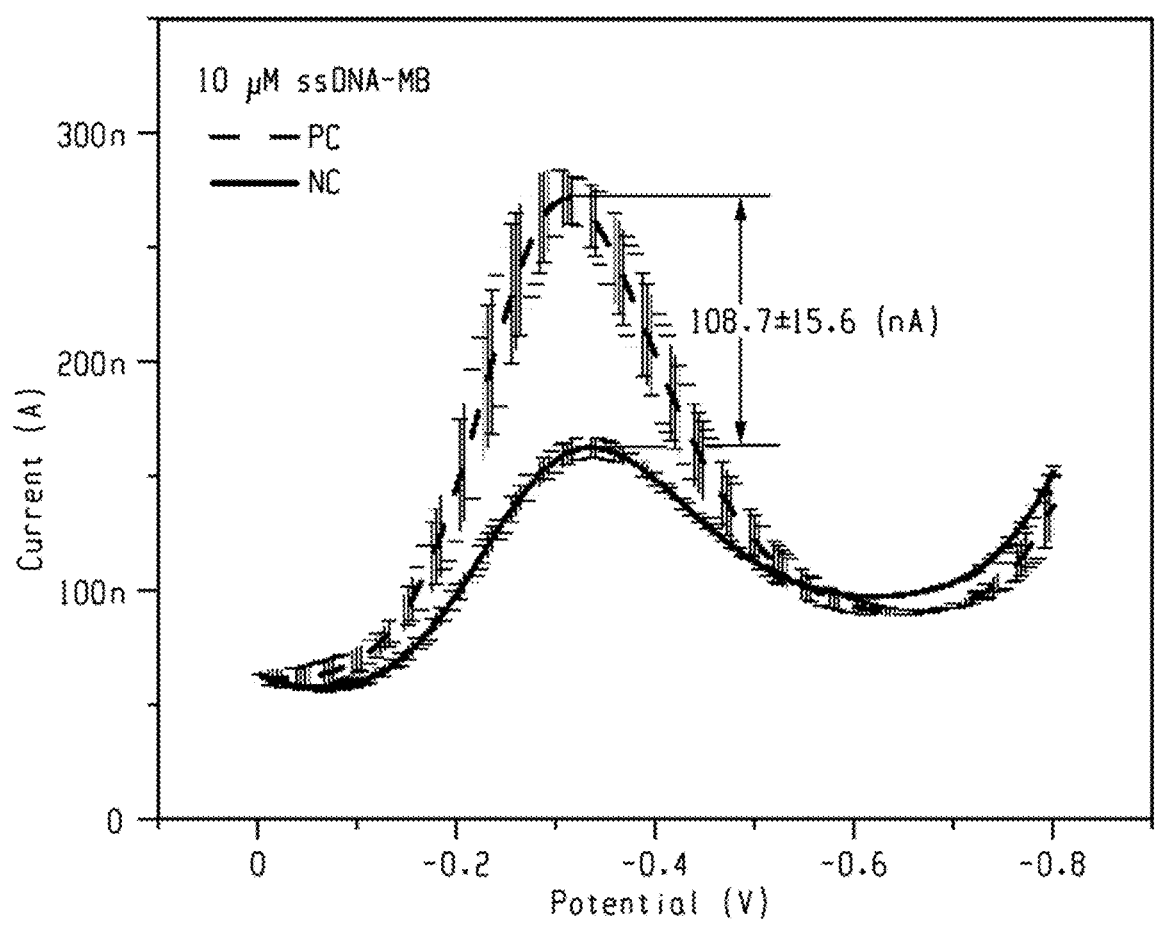
Figure 3E:
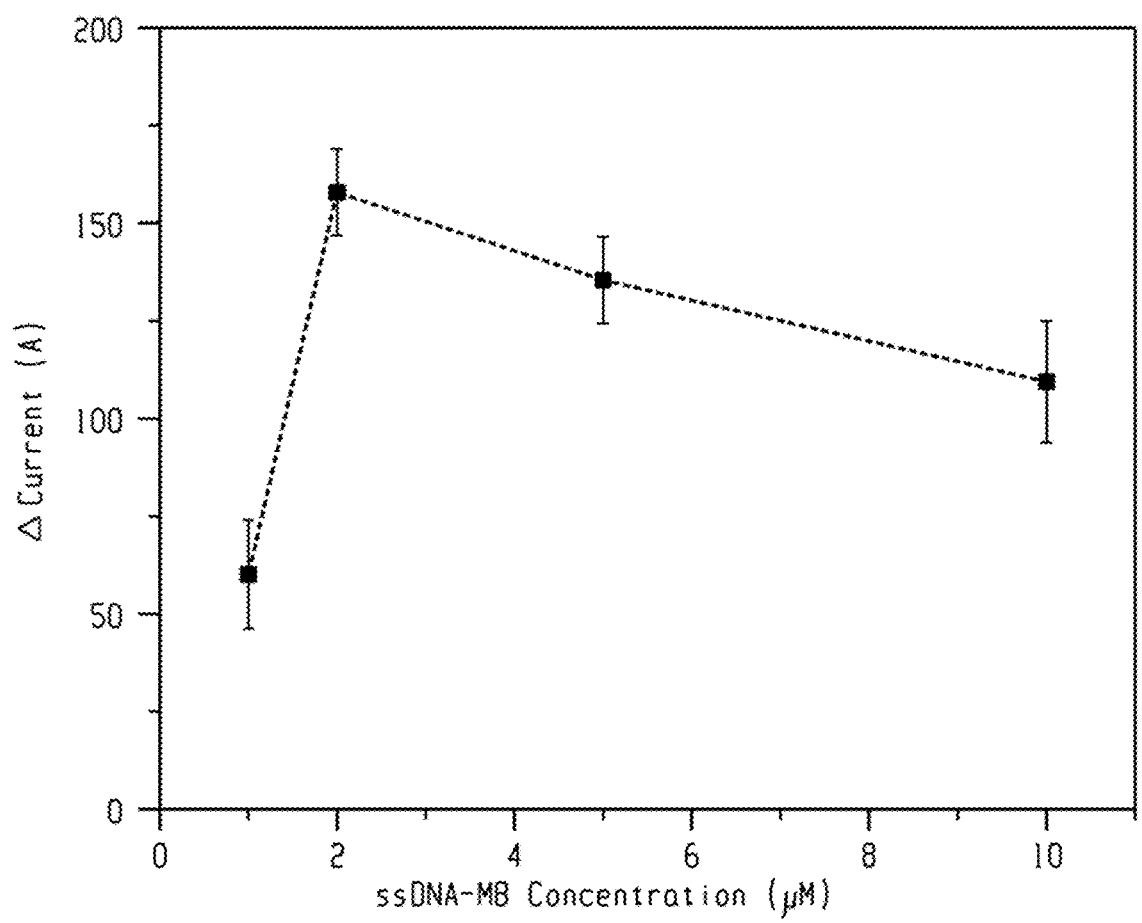

Pulsed Electric Field Generation. During on-chip CRISPR-based detection, pulsed electric fields (FIG. 2) were generated by Trueform Series Waveform Generators 33520B (Keysight Technologies, CA, USA). The pulsed electric field was applied to the electrochemical CRISPR biosensor, where the working electrode served as a positive electrode and the reference/counter electrodes served as ground electrodes.

Electrochemical Detection. For on-chip electrochemical detection, the ssDNA-FQ was replaced by electroactive ssDNA-MB probes and the electrochemical signals were detected at the end of the CRISPR reactions (e.g., 60 minutes). All electrochemical signal detections were performed on a CHI660D potentiostat (CH Instruments, TX, USA). Differential pulse voltammetry (DPV) was applied to determine the redox peak current.

Clinical Sample Preparation and HPV-16 DNA Detection. De-identified clinical vaginal swab samples were obtained from the Hospital of the University of Pennsylvania and approved by its ethics committee (IRB protocol: #829760). HPV DNA was extracted from clinical samples by the DNeasy® Blood & Tissue Kit according to the manufacturer's protocol. Briefly, 200 µL clinical vaginal swab samples were centrifuged at 1,000×g for 10 minutes to remove the liquid supernatant. The concentrated cells were washed three times with phosphate buffered saline (PBS) and resuspended in 200 µL PBS, mixed with 20 µL proteinase K and 200 µL buffer AL (DNeasy® Blood and Tissue Kit), and then incubated at 56° C. for 10 minutes. The lysate was mixed with 200 µL ethanol and introduced into the DNeasy® Mini spin column for nucleic acid extraction and purification. Subsequent to the sample introduction, 500 µL of QIAGEN® wash buffer 1 (AW1) and QIAGEM® wash buffer 2 (AW2) were, respectively, added into the spin column to remove any remaining amplification inhibitors. Then, the DNA was eluted by adding 200 µL Buffer AE.

For clinical sample detection, the HPV-16 DNA extracts were first pre-amplified by RPA amplification at 37° C. The 25 µL RPA reaction solution contained 1× reaction buffer, 1× basic E-mix, 1× core reaction buffer, 14 mM MgOAc, 0.32 µM each of forward and reverse primers, 0.8 mM of each nucleotide (dATP, dTTP, dCTP, dGTP), and 2 µL DNA extracts. After RPA amplification, 2 µL amplicons were used for electrochemical CRISPR detection on the EFE electrochemical CRISPR biosensor.

Figure 1B:
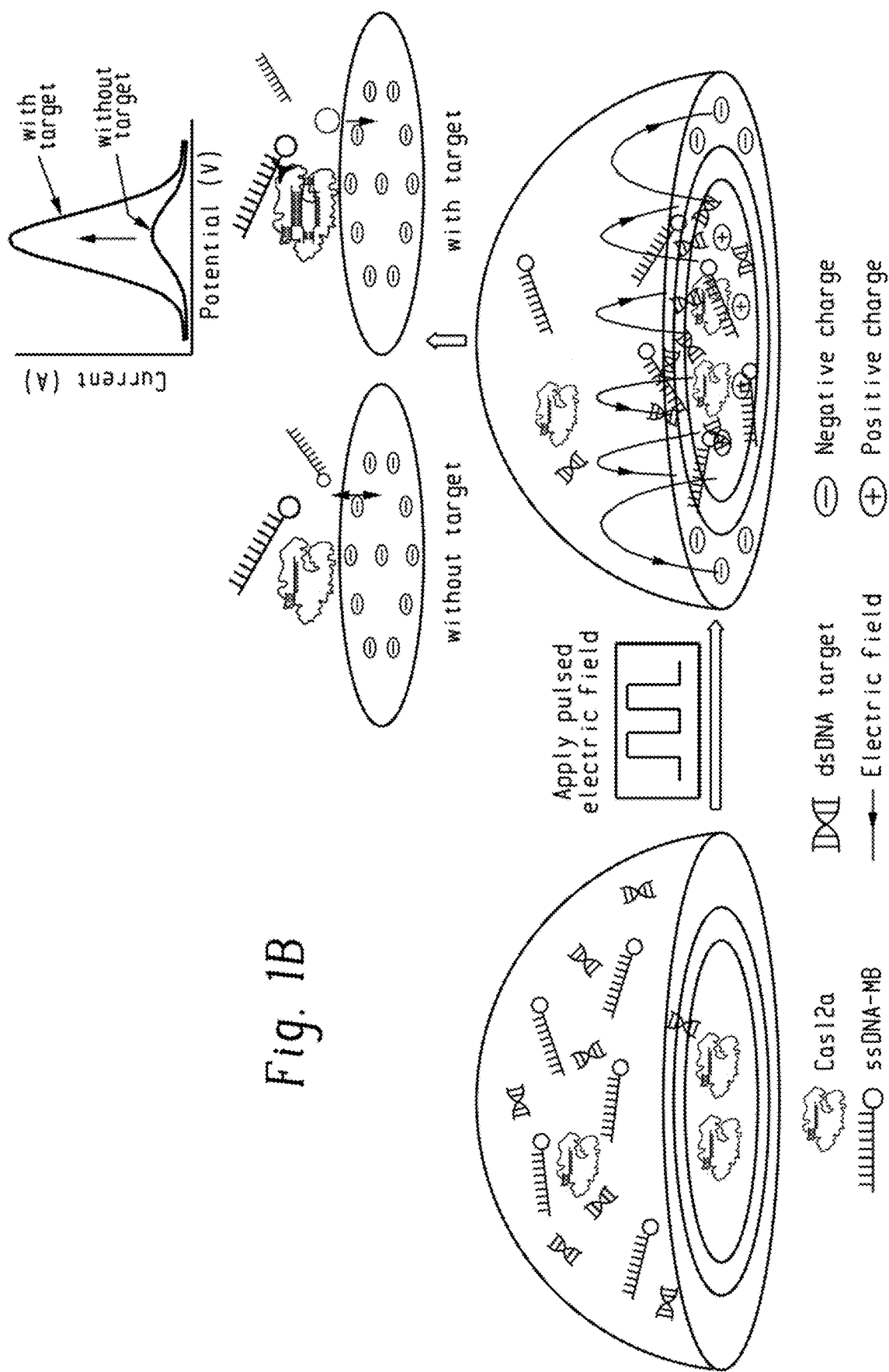

Electrical Field-Enhanced (EFE) Electrochemical Crispr Biosensor. As mentioned above, the working principle of the EFE, immobilization-free, electrochemical CRISPR biosensor of the present disclosure is schematically illustrated in FIGS. 1A and 1B. As shown in FIG. 1A, the CRISPR- Cas12a protein has both cis-cleavage activity (target DNA cutting) and trans-cleavage activity (ssDNA cutting). To enhance the electrochemical detection sensitivity, the CRISPR biosensor of the present disclosure uses a pulsed electric field to enrich DNAs (e.g., target DNA, ssDNA-MB) on the positively charged surface of the working electrode (first two panels of FIG. 1B) due to the negative charge of the DNA molecules. In the absence of the target DNA, the ssDNA-MB probe is electrostatically repelled from the negatively charged electrode during differential pulse voltammetry detection (potential range of −0.6 to 0 V) because the DNA itself is negatively charged, which leads to a low electrochemical current on the working electrode (last panel of FIG. 1B). On the contrary, in the presence of the target DNA, the CRISPR-Cas12a protein is specifically activated and non-specifically cuts ssDNA-MB due to its trans-cleavage activity, releasing the CRISPR-cleaved, electroactive MB probes. Due to decreased negative charge and smaller size, the CRISPR-cleaved electroactive MB probe has higher diffusivity toward and reduced electrostatic repulsion from the negatively charged electrode surface than that of the ssDNA-MB probes, which results in an increased electrochemical signal (last panel of FIG. 1B). Unlike previously reported electrochemical CRISPR biosensors, CRISPR biosensor of the present disclosure performs electrochemical detection of DNA targets in a homogeneous solution, which not only eliminates the need for complicated probe immobilization on the electrode surface, but also improves the reaction efficiency. Thus, the EFE electrochemical CRISPR biosensor of the present disclosure provides a simple, highly sensitive, immobilization-free, electrochemical DNA detection strategy.

Example 1: Optimization of the ssDNA-Methylene Blue Probe Concentration. MB has been widely used either as an electrochemical hybridization indicator or as an electroactive probe for DNA strands in electrochemical DNA detection due to its high sensitivity and electrochemical activity. In the ssDNA-MB probe of the present disclosure, the MB molecule is modified on or attached to the end of the ssDNA oligonucleotides, which provides the electrostatic force due to its negative charge in our EFE electrochemical CRISPR biosensor. The electroactive ssDNA-MB probe consists of a five-mer single-strand DNA and an MB tag labeled at the 3' terminus (Table 1). The amount of ssDNA-MB probe was optimized by evaluating different ssDNA-MB probe concentrations ranging from 1 to 10 µM. As shown in FIGS. 3A-3E, the concentration of 2 µM ssDNA-MB probes showed the best signal-to-background ratio (157.5±11.0 nA). Interestingly, further increasing the ssDNA-MB probe concentration reduced the electrochemical current difference. This result was attributed to increased background signals because more ssDNA-MB probes would diffuse to the electrode surface by overcoming the electrostatic repulsion at high probe concentrations. Therefore, the 2 µM concentration of the ssDNA-MB probe was used in all subsequent experiments due to its optimal signal-to-background ratio.

Figure 4A:
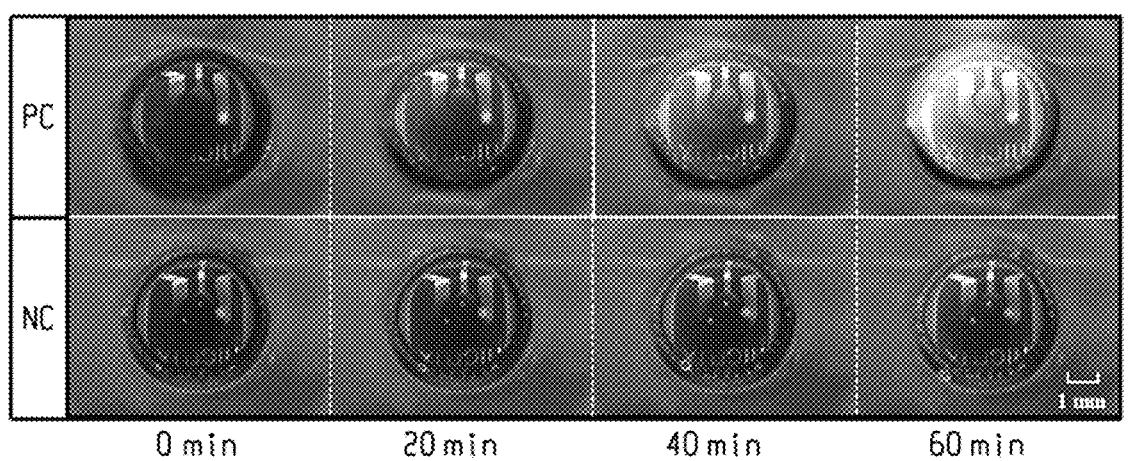
FIGS. 4A, 4B, and 4C. Optimization of the pulsed electric field for CRISPR-based DNA detection.
Figure 4B:
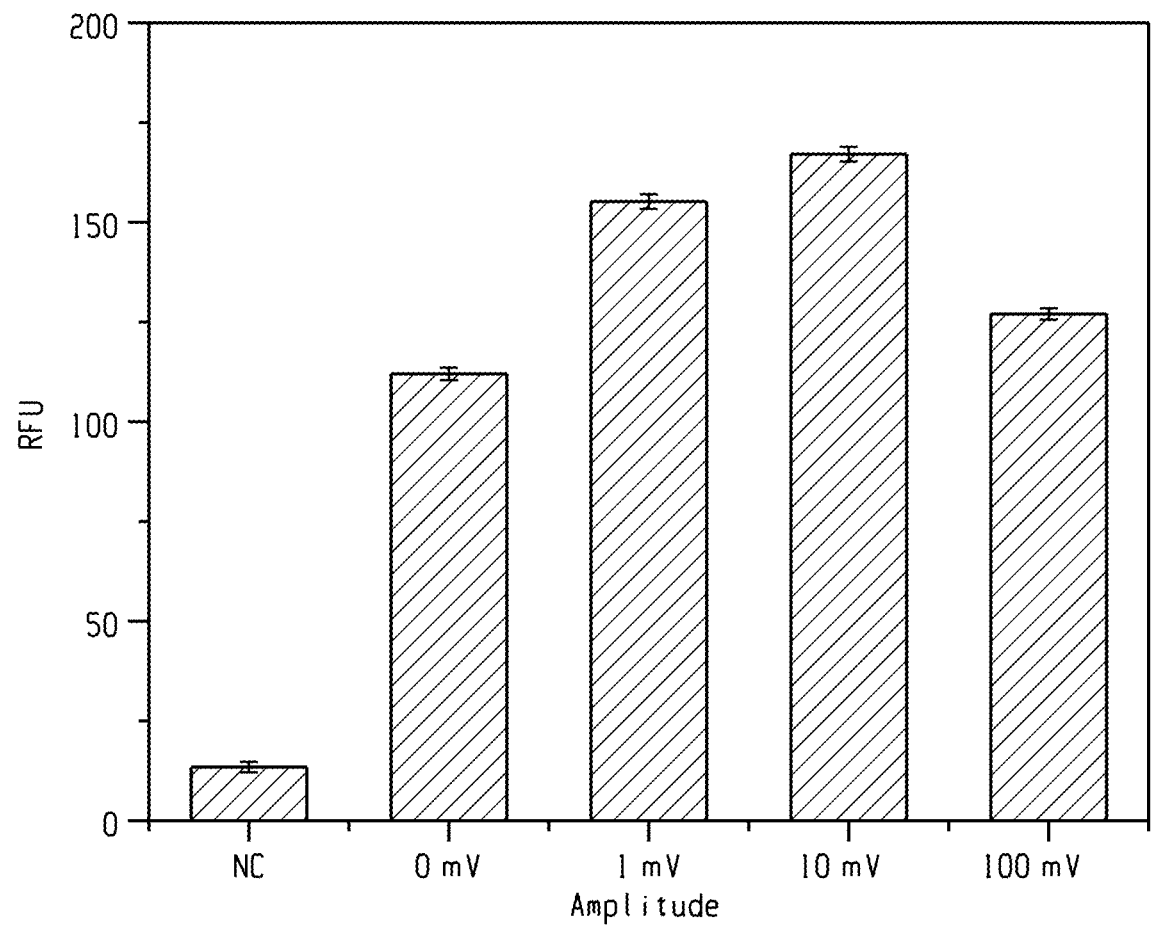
Figure 4C:
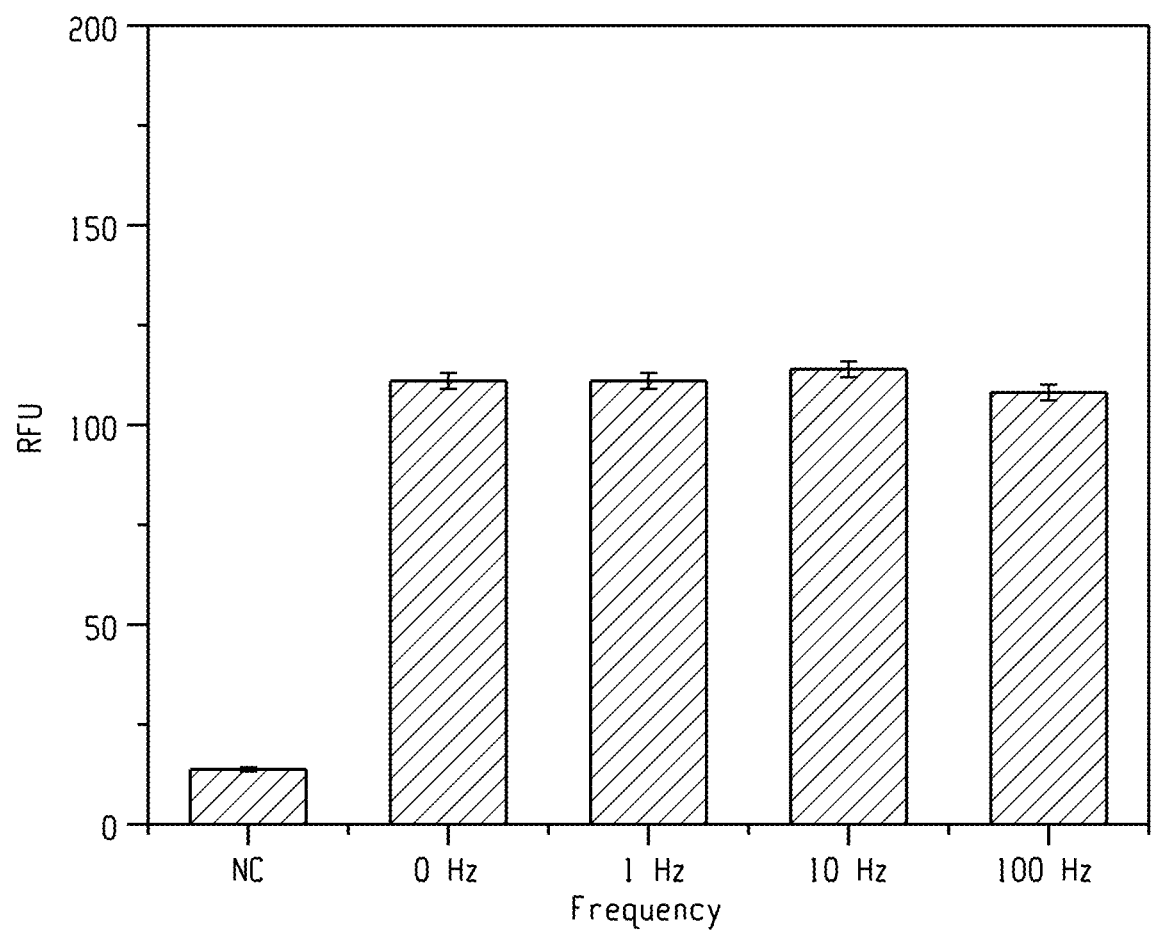
Figure 5A:
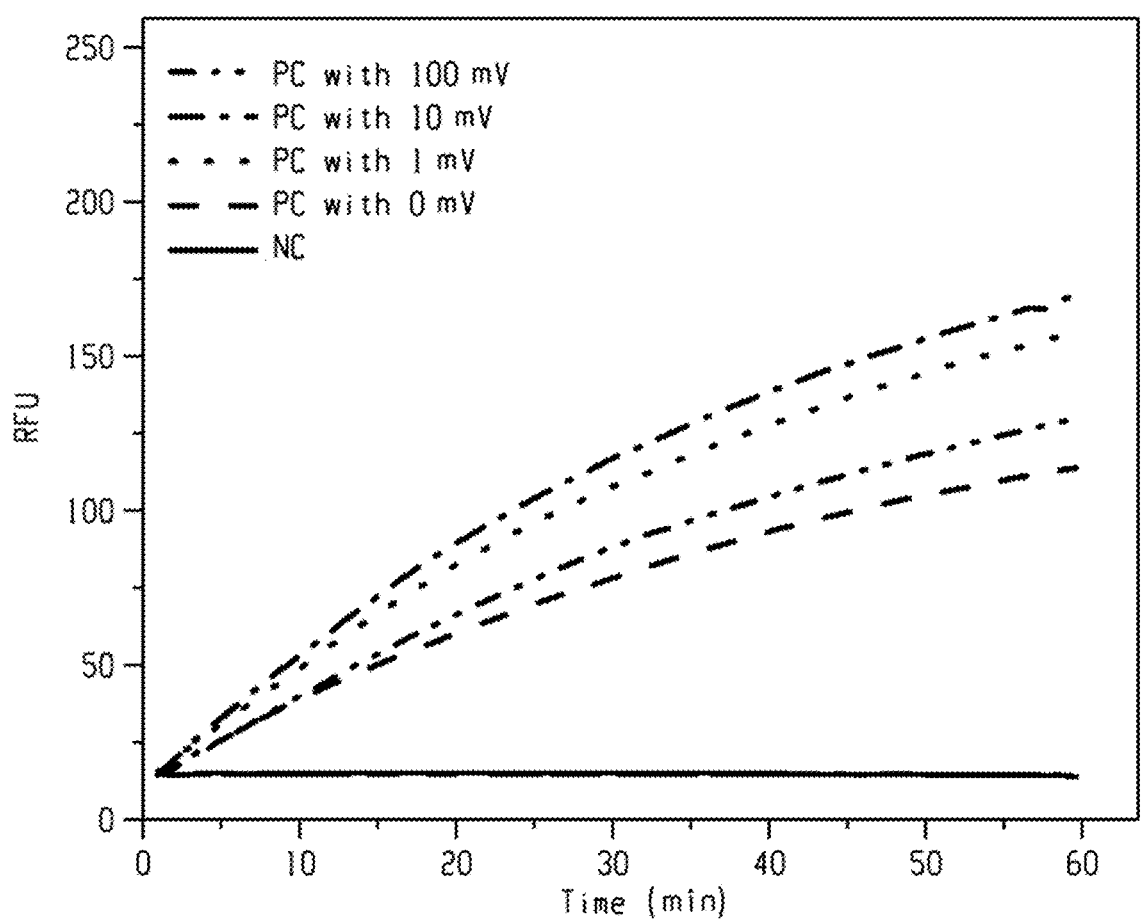
FIGS. 5A and 5B.
Figure 5B:
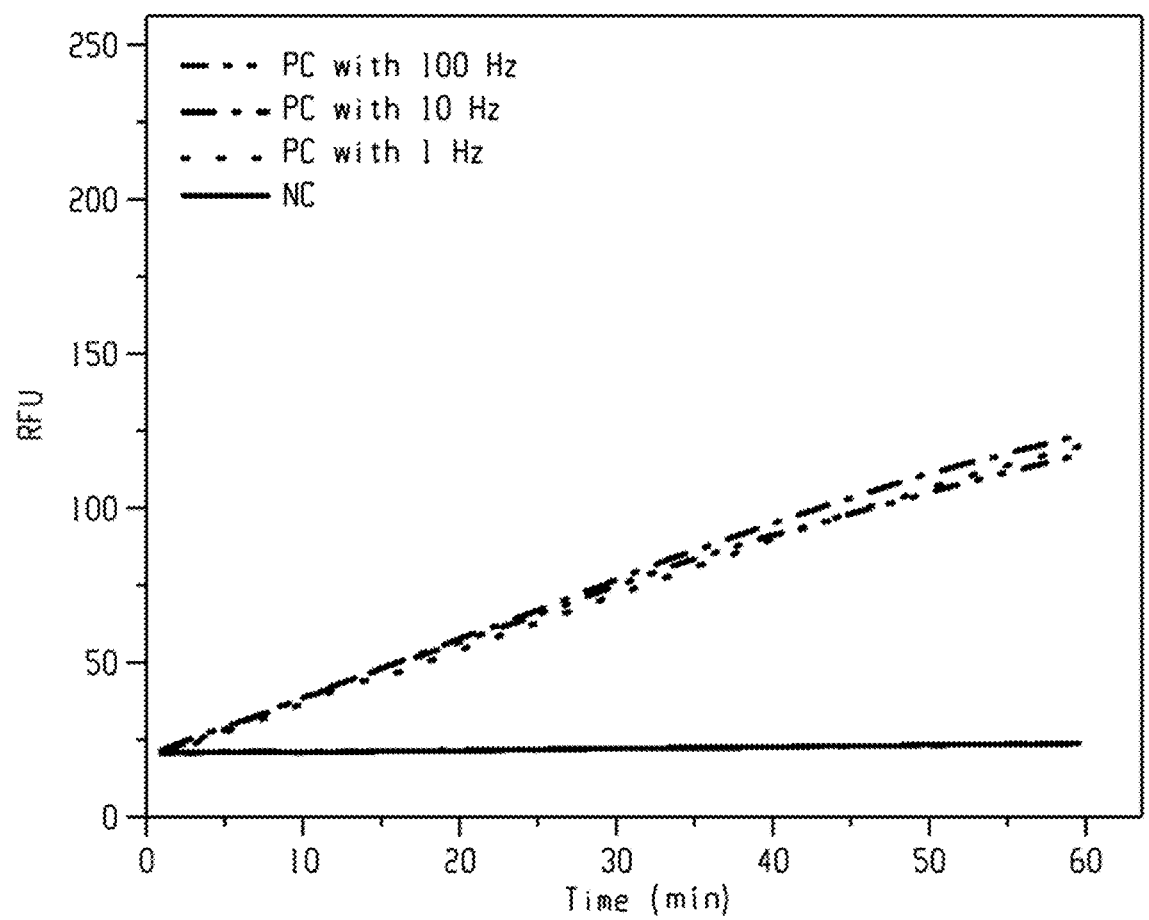

Example 2: Optimization of the Pulsed Electric Field. Previous research indicates that the electric field provides an ideal strategy for DNA manipulation and concentration with different electric waveforms. Here, a pulsed electric field (FIG. 2) was applied to the electrochemical electrodes during the CRISPR-based detection. The pulsed electric field consisted of an AC electric field and a DC offset. The offset potential was set to half of the peak-to-peak potential (i.e., the amplitude of the electric field) and the pulse width as 50% of T (i.e., the period). To facilitate real-time monitoring of the CRISPR detection signal during pulsed electric field optimization, a portable Dino-Lite digital fluorescence microscope was used to record the fluorescence images of the CRISPR reaction solution in the electrochemical chamber (FIG. 4A). First, we determined the effects of different peak-to-peak potential values ranging from 0 to 100 mV on the CRISPR biosensor. As shown in FIG. 4B and FIG. 5A, we found that the higher the peak-to-peak amplitude, the stronger the fluorescence signals of the CRISPR detection, thus demonstrating that the pulsed electric field can enrich the DNA and accelerate CRISPR detection. However, when the peak-to-peak amplitude reached 100 mV, the fluorescence signal decreased, which may be attributed to the redox reaction on the electrode surface when relatively high voltage is applied. In our experiment, a peak-to-peak amplitude of 10 mV resulted in the strongest fluorescence signals. Next, we investigated the effects of the frequency of the pulsed electric field. As shown in FIG. 4C and FIG. 5B, we observed no significant difference when we applied various frequencies (from 1 Hz to 100 Hz). Therefore, we utilized the optimized pulsed electric field with a peak-to-peak amplitude of 10 mV and a frequency of 1 Hz for all subsequent experiments.

Figure 6A:
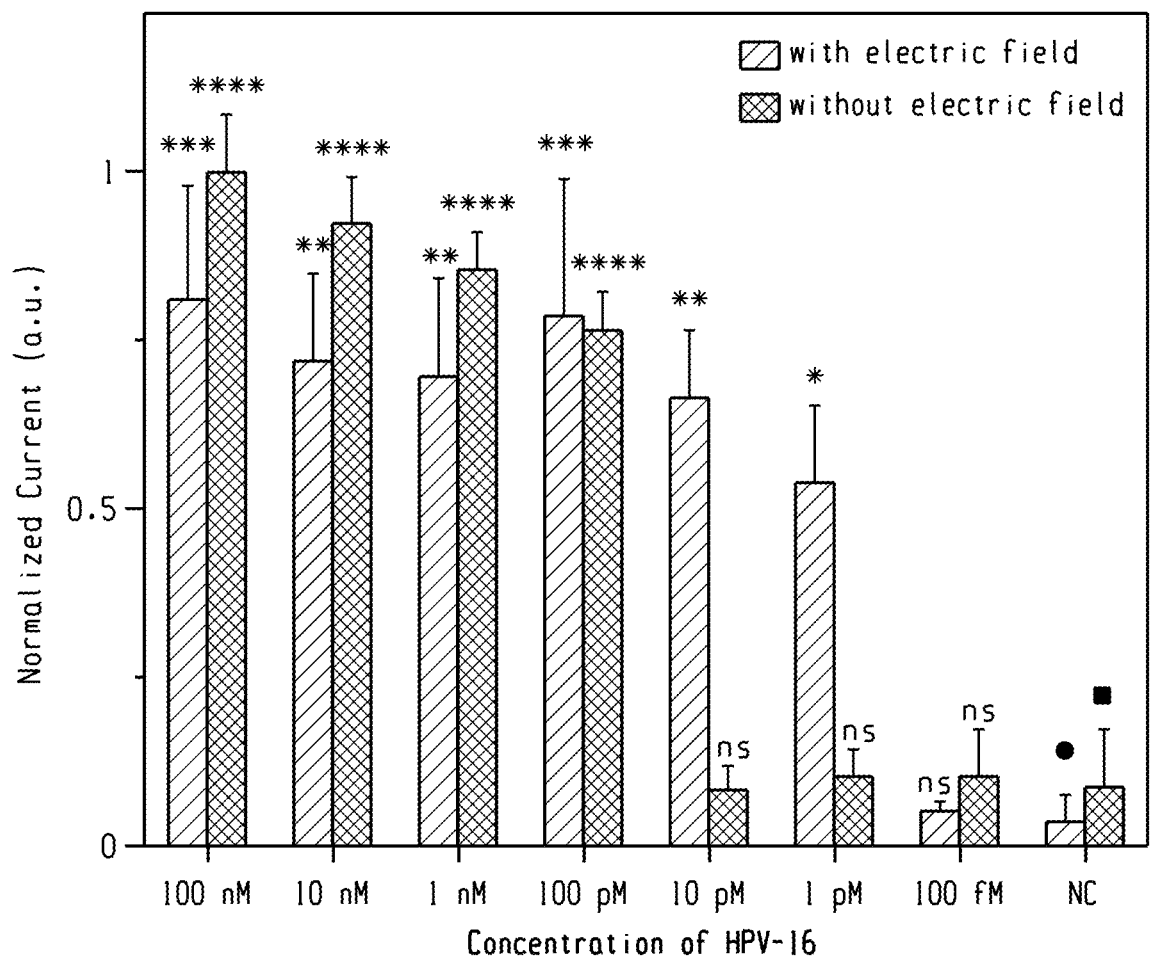
FIGS. 6A and 6B. Comparison of Human Papillomavirus (HPV)-16 DNA detection by the EFE electrochemical CRISPR biosensor with and without applying a pulsed electric field, as well as real-time CRISPR fluorescent detection.
Figure 6B:
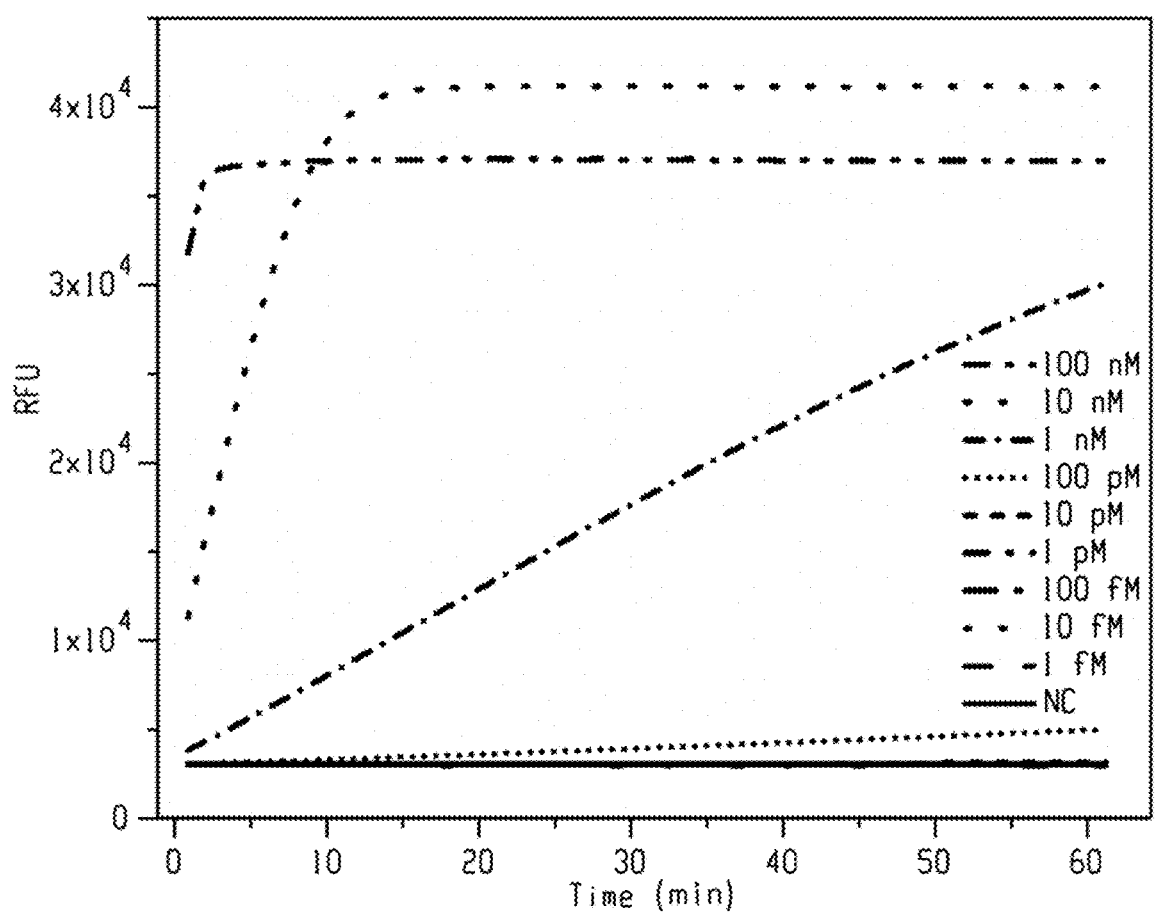

Example 3: Analytical Performance of the EFE Electrochemical Crispr Biosensor. Under the optimized experimental conditions, the analytical sensitivity of the EFE electrochemical CRISPR biosensor was determined by directly detecting a tenfold serial dilution of unamplified HPV-16 DNA. For comparison, the analytical performance of the electrochemical CRISPR biosensor was evaluated with and without the pulsed electric field applied. As shown in FIG. 6A, without applying a pulsed electric field, the electrochemical CRISPR biosensor could detect 100 pM of HPV-16 DNA target, which is comparable to that of the conventional CRIPSR-based fluorescence detection in the reaction tubes as shown in FIG. 6B. On the contrary, when we applied the pulsed electric field, the electrochemical CRISPR biosensor consistently detected 1 pM of HPV-16 DNA target, which is 100 times higher than when the pulsed electric field was not applied. In addition, compared with previous electrochemical CRISPR biosensors with immobilized probes, the EFE electrochemical CRISPR biosensor showed 50 times higher sensitivity in the detection of unamplified HPV-16 DNA. The improved sensitivity of our CRISPR biosensor can be attributed to electric field-assisted DNA enrichment induced by the pulsed electric field. Therefore, applying the pulsed electric field significantly improves the detection sensitivity of the electrochemical CRISPR biosensor for DNA detection.

Figure 7A:
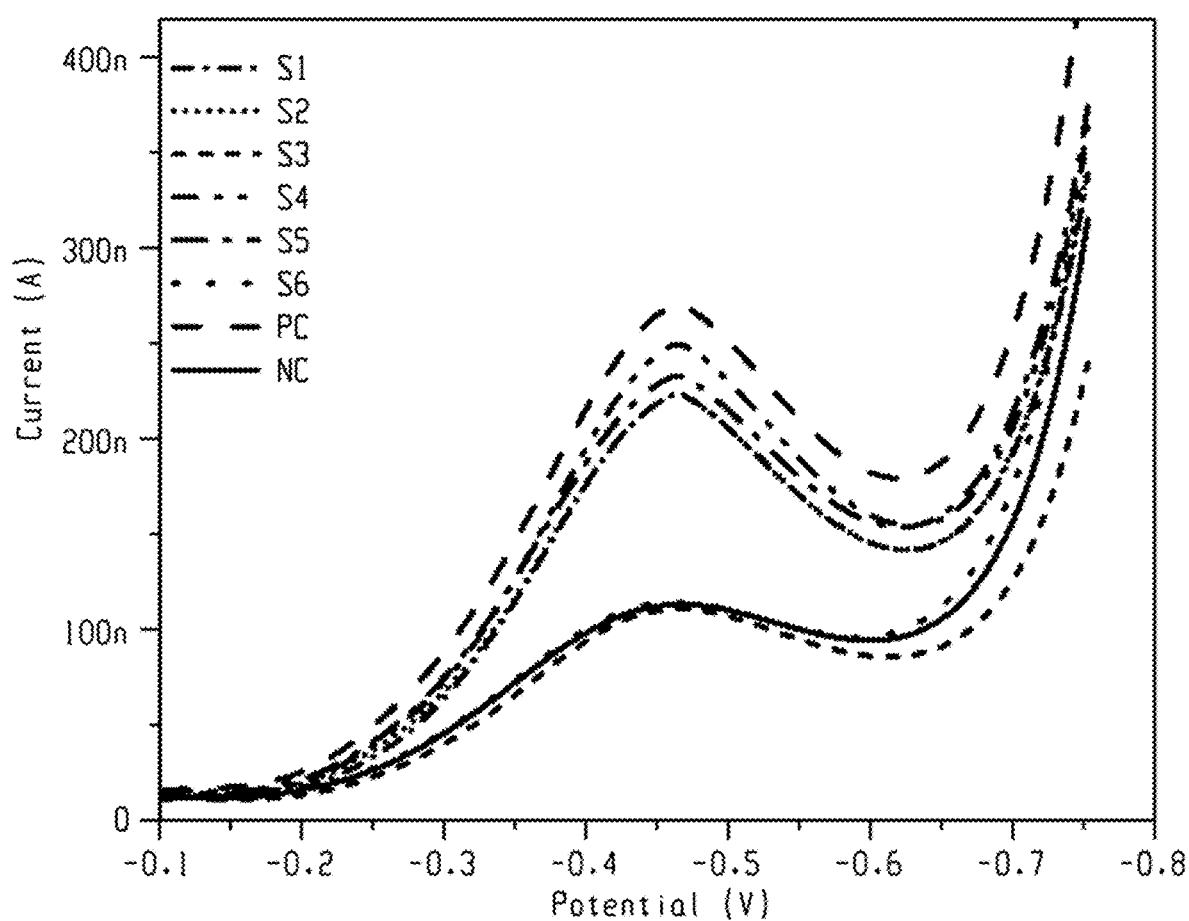
FIGS. 7A and 7B. HPV-16 DNA detection in clinical samples by using the EFE electrochemical CRISPR biosensor after RPA pre-amplification.
Figure 7B:
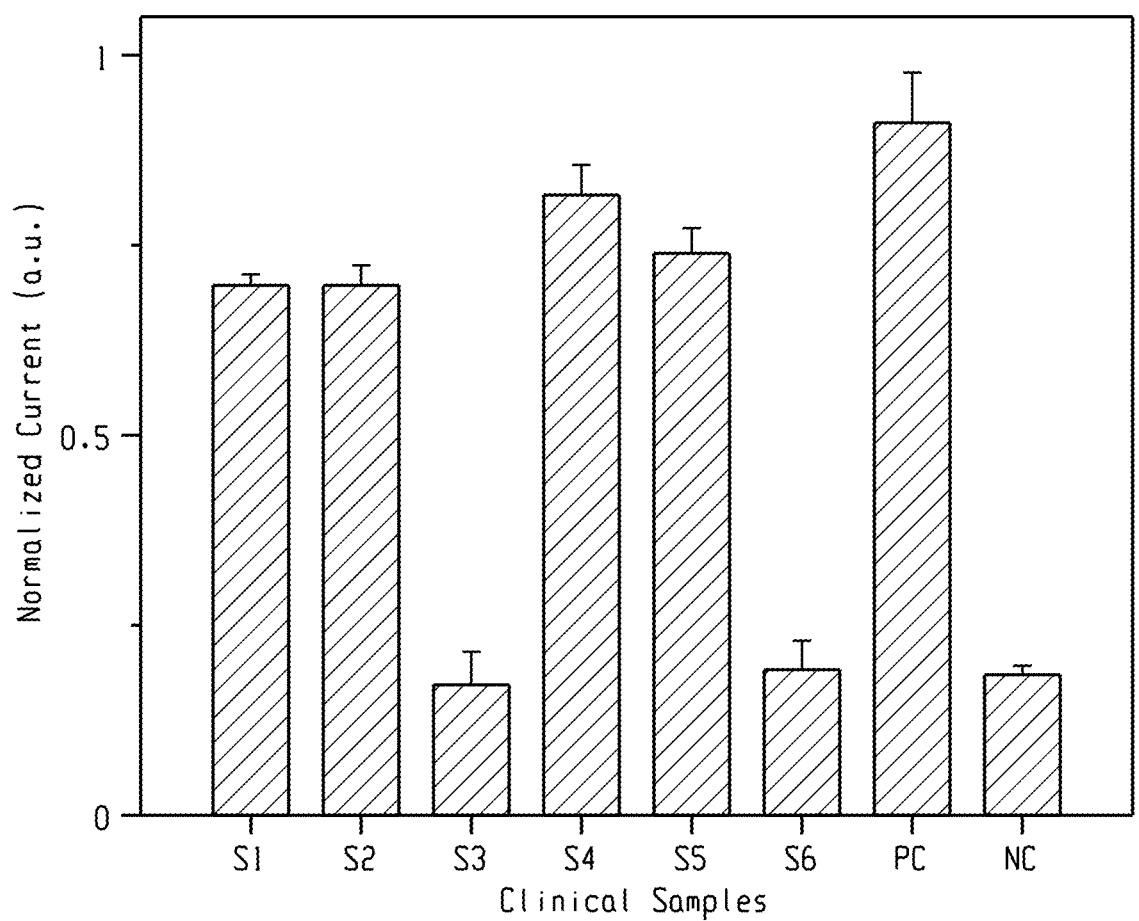
Figure 8A:
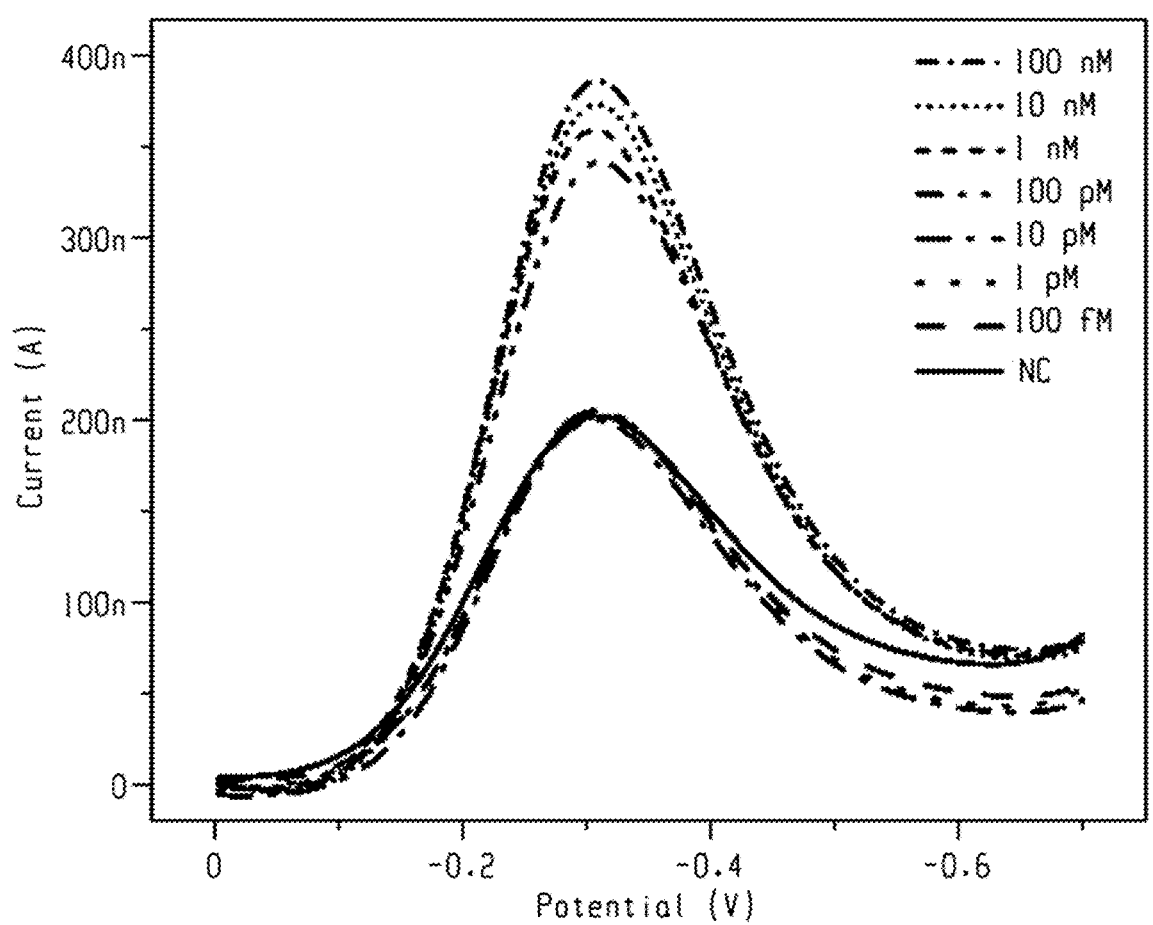
FIGS. 8A and 8B. Comparison of HPV-16 DNA detection by electrochemical CRISPR biosensor with or without pulsed electric field.
Figure 8B:
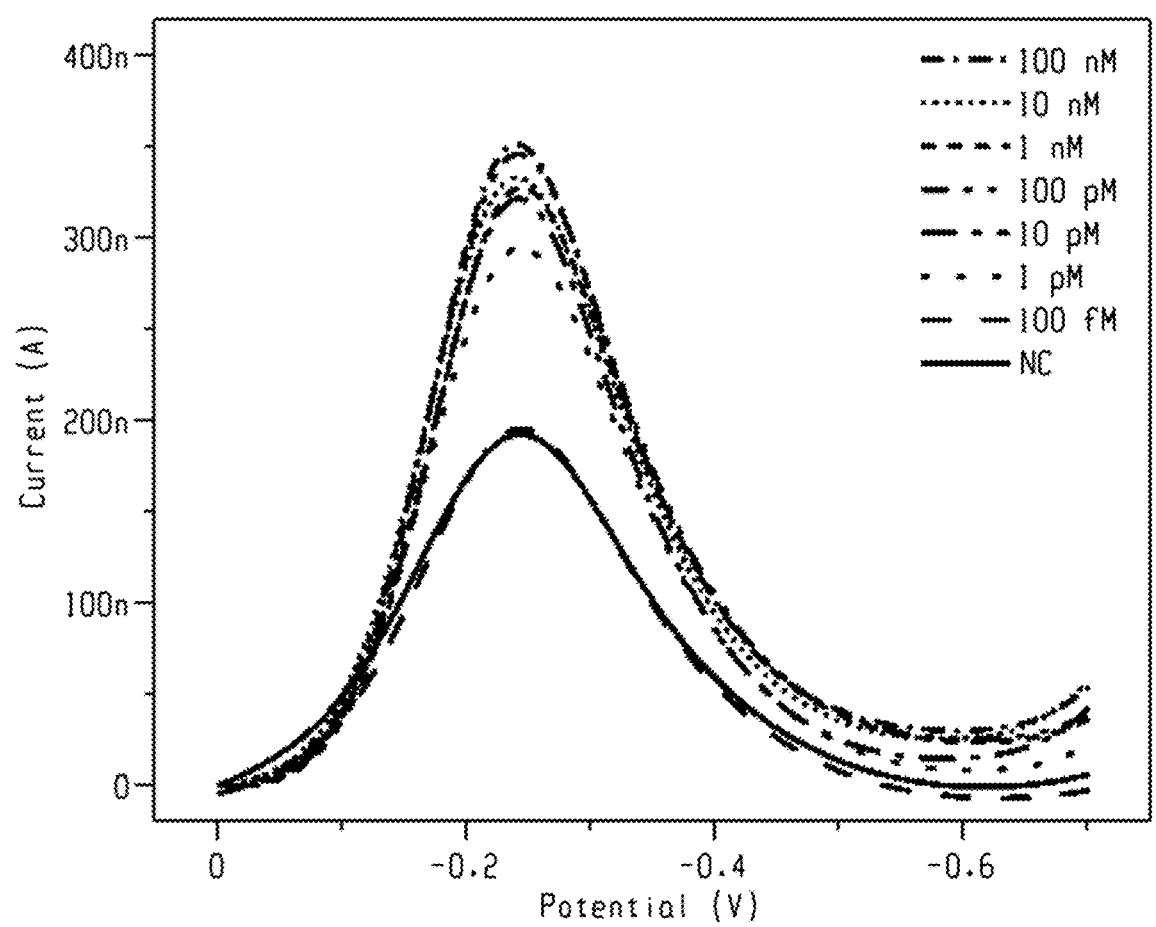
Figure 9A:
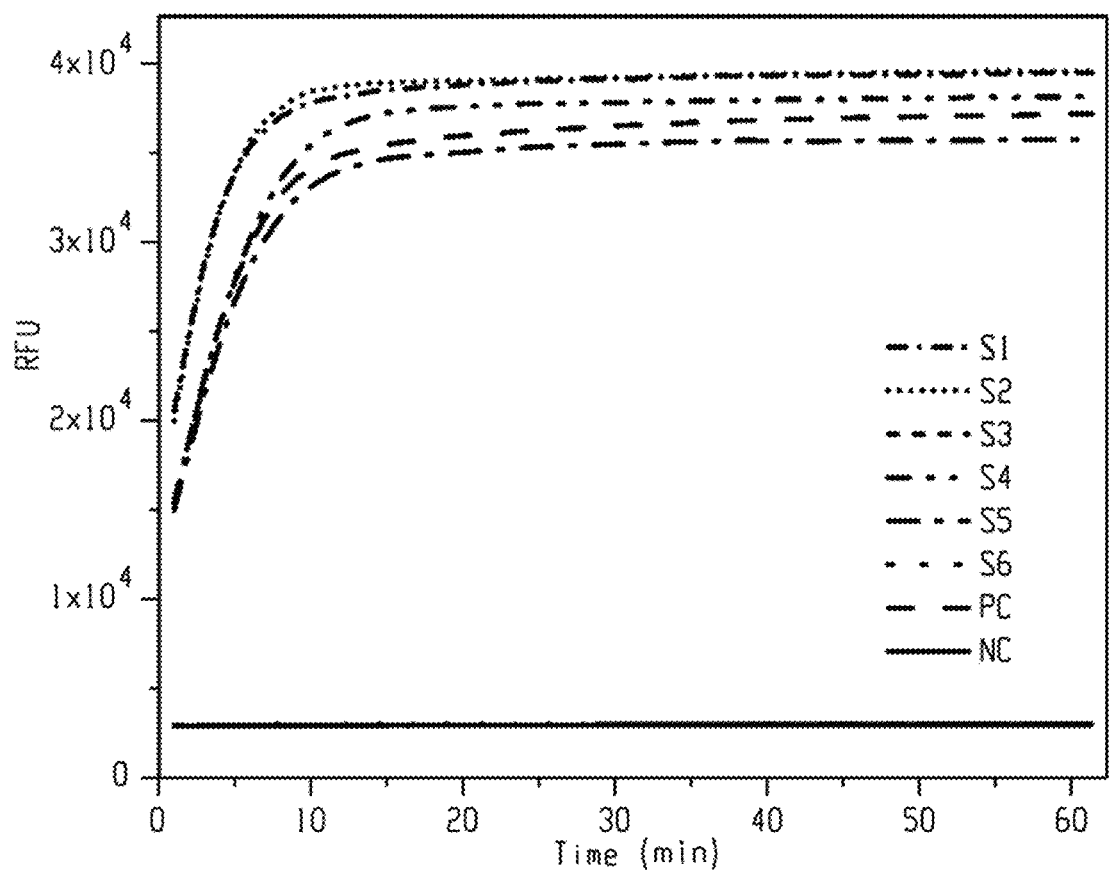
FIGS. 9A, 9B, and 9C. CRISPR-based florescence detection of HPV-16 DNA in clinical samples after RPA pre-amplification.
Figure 9B:
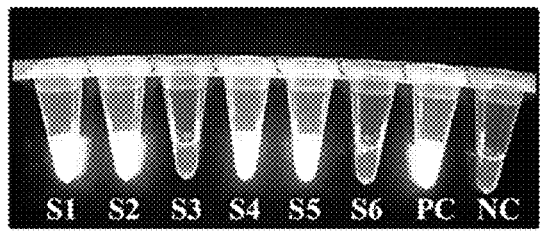
Figure 9C:
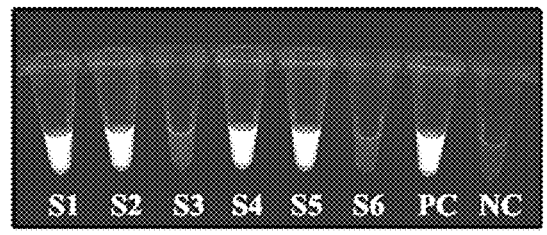

Example 4: Clinical Validation of the EFE Electrochemical Crispr Biosensor. HPV-16 is the most prevalent genotype in HPV-associated cancers, including cervical cancer. To validate the clinical utility of the EFE electrochemical CRISPR biosensor, clinical swab samples, including two negative samples and four positive samples, were examined for HPV-16 DNA detection. To meet clinical requirements, the HPV-16 DNA samples extracted from clinical swab samples were pre-amplified by RPA amplification before performing electrochemical detection. As shown in FIG. 7A, FIG. 7B, FIG. 8A, and FIG. 8B, all four positive clinical samples consistently showed a higher electrochemical peak in their DPV curves, which was not the case for the two negative samples. For comparison, the HPV-16 DNA samples were tested using conventional CRISPR-based fluorescence detection in the reaction tubes after RPA pre-amplification (FIGS. 9A, 9B, and 9C), which showed results consistent with those of the EFE electrochemical CRISPR biosensor (FIG. 7A and FIG. 7B). Therefore, the EFE electrochemical CRISPR biosensor described herein is suitable for clinical diagnostic applications in the detection of HPV-associated cancer and other infectious diseases.

Discussion of the Examples. A simple, sensitive, and versatile electrochemical CRISPR biosensor for DNA detection in homogeneous solutions was developed by combining electric field-assisted DNA enrichment with a CRISPR-based assay. Compared to previous electrochemical CRISPR biosensors, the EFE electrochemical CRISPR biosensor as described herein offers several advantages. For example, by leveraging the pulsed electric field, the developed electrochemical CRISPR biosensor can detect 1 pM HPV-16 DNA target without amplification, which is 100 times more sensitive than conventional electrochemical CRISPR detection. Furthermore, unlike existing electrochemical CRISPR biosensors, the biosensor described herein enables CRISPR-Cas12a cleavage in a homogeneous solution phase rather than the heterogeneous electrode/solution interface, which improves the CRISPR detection efficiency by minimizing steric hindrance of the immobilized probes and eliminates the need for the tedious probe immobilization process. Additionally, by coupling the EFE electrochemical CRISPR biosensor described herein with isothermal amplification, increased sensitive can be accomplished such that the EFE electrochemical CRISPR biosensor can detect HPV-16 DNA in clinical samples, enabling simple and sensitive point-of-care molecular diagnostics. To further simplify the operation of the CRISPR biosensor, the CRISPR biosensing methodology described herein can be adapted to a "one-pot" RPA/CRISPR assay. Therefore, the EFE electrochemical biosensor described herein represents a significant step forward in the realization of a simple, portable, and affordable electrochemical DNA detection system and method for clinical applications at the point of care.

Definitions

The following terms are used to describe the invention of the present disclosure. In instances where a term is not specifically defined herein, that term is given an art-recognized meaning by those of ordinary skill applying that term in context to its use in describing the present disclosure.

The use of the terms "a" and "an" and "the" and similar referents (especially in the context of the following claims) are to be construed to cover both the singular and the plural, unless otherwise indicated herein or clearly contradicted by context. By way of example, "an element" means one element or more than one element.

It should also be understood that, in certain methods described herein that include more than one step or act, the order of the steps or acts of the method is not necessarily limited to the order in which the steps or acts of the method are recited unless the context indicates otherwise. Furthermore, the terms first, second, etc., as used herein are not meant to denote any particular ordering, but simply for convenience to denote a plurality of, for example, layers.

The terms "comprising", "having", "including", and "containing" are to be construed as open-ended terms (i.e., meaning "including, but not limited to") unless otherwise noted.

The terms "about" or "approximately," as used herein, is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±10% or 5% of the stated value. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "one or more," as used herein, means at least one, and thus includes individual components as well as mixtures/combinations of the listed components in any combination.

Other than in the operating examples, or where otherwise indicated, all numbers expressing quantities of ingredients and/or reaction conditions are to be understood as being modified in all instances by the term "about," meaning within 10% of the indicated number (e.g., "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

What is claimed is:

1. An immobilization-free, electrochemical method of detecting a target deoxyribonucleic nucleic acid (DNA) sequence in a sample, the method comprising:
    incubating the sample with a detection mixture that comprises:
        (i) a nucleic acid probe that has a negative charge and that includes a single-stranded DNA (ssDNA) sequence that hybridizes with a nucleic acid sequence of the target DNA sequence covalently linked to an electroactive probe, wherein the electroactive probe has a neutral or positive charge;
        (ii) a Class 2 cluster regularly interspaced short palindromic repeats (CRISPR)-associated (Cas) protein or enzyme that has trans-cleavage activity for ssDNA; and
        (iii) a guide ribonucleic acid (gRNA) that includes
            (A) a scaffold sequence that interacts with the Class 2 Cas protein, and
            (B) a nucleic acid sequence that hybridizes with a sequence of the target DNA sequence;
    applying an electric field comprising an alternating current (AC) electric field and a direct current (DC) offset to the detection mixture to concentrate nucleic acids in the sample and the nucleic acid probe on a positively charged working electrode, wherein the electroactive probe is released from the nucleic acid probe by the Class 2 Cas protein when the target DNA sequence is present in the detection mixture; and
    measuring, after applying the electric field, a current of the detection mixture as potential is applied, wherein detection of a current in the detection mixture indicates the presence of the target DNA sequence in the sample.

2. The method of claim 1, wherein:
    the electroactive probe has a neutral charge or a positive charge;
    the electroactive probe is located on the 5' end of the ssDNA sequence of the nucleic acid probe that hybridizes with a nucleic acid sequence of the target DNA sequence, the 3' end of the ssDNA sequence that hybridizes with a nucleic acid sequence of the target DNA sequence, or both; or
    a combination thereof.

3. The method of claim 1, wherein the electroactive probe is methylene blue, the Class 2 Cas protein is CRISPR-Cas12a, or both.

4. The method of claim 1, wherein:
    incubating the sample with the detection mixture includes incubating at about 35° C. to about 42° C.;
    incubating the sample with the detection mixture is performed for about 10 to about 90 minutes;
    the electric field is applied for about 10 to about 90 minutes while or prior to measuring the current of the detection mixture; or
    a combination thereof.

5. The method of claim 1, wherein:
    the electric potential of the AC electric field is about 0.1 millivolts (mV) to about 100 mV;
    the electric potential of the DC offset is about 0.10% to about 90% of the electric potential of the AC electric field; or
    a combination thereof.

6. The method of claim 1, wherein:
    the frequency (f) of the electric field is about 1 hertz (Hz) to about 100 Hz;
    the period of the electric field (T) is about (0.05×f) to about (2.0×f);
    the electric field has a pulse width that is about (0.10× T) to about (0.95× T); or
    a combination thereof.

7. The method of claim 1, wherein the target DNA sequence is a positive control nucleic acid sequence, or the target DNA sequence is a nucleic acid sequence from at least one of a mutation, a genotype, a cancer, an infectious agent, a pathogen, a microorganism, a disease, disorder, or condition associated with the target DNA sequence, or a combination thereof.

8. The method of claim 1, wherein the method detects 200 or more copies of the target DNA sequence.

9. The method of claim 1, wherein:
    the nucleic acid sequence that hybridizes with a sequence of the target DNA sequence is about 10 base pairs to about 30 base pairs long;
    the ssDNA sequence of the nucleic acid probe that hybridizes with a nucleic acid sequence of the target DNA sequence is about 4 base pairs to about 20 base pairs long;
    the gRNA is about 35 to about 50 base pairs long; or
    a combination thereof.

10. The method of claim 1, wherein the method is performed in a reaction chamber of an electrochemical sensor, a single solution, a homogeneous solution, or a combination thereof.

11. The method of claim 1, further comprising amplifying the target DNA sequence in the sample incubating, wherein the sample incubated with the detection mixture is an amplification product, or a portion thereof.

12. The method of claim 11, wherein amplifying the target DNA sequence in the sample includes performing a recombinase polymerase amplification (RPA) reaction, wherein at least one of:
    the nucleic acid sequence that hybridizes with a sequence of the target DNA sequence is about 15 base pairs to about 30 base pairs long;
    the ssDNA sequence of the nucleic acid probe that hybridizes with a nucleic acid sequence of the target DNA sequence is about 4 base pairs to about 20 base pairs long;
    incubating the amplification product, or a portion thereof, is performed at about 35° C. to about 40° C.;
    the RPA reaction is performed at about 35° C. to about 42° C.;
    the gRNA is about 35 to about 50 base pairs long;
    the RPA reaction is an isothermal amplification;
    the RPA reaction is about 10 minutes to about 60 minutes; or
    a combination thereof.

13. The method of claim 11, wherein the method detects 100 copies or more of the target DNA sequence.

14. The method of claim 11, wherein the method is performed in a reaction chamber of an electrochemical sensor, a single solution, a homogeneous solution, or a combination thereof.

15. The method of claim 1, wherein the detection mixture further comprises reagents for a recombinase polymerase amplification (RPA) reaction.

16. The method of claim 15, further comprising performing a RPA reaction to amplify the target DNA sequence.

17. The method of claim 1, wherein the method further comprising performing a reverse transcription reaction to produce the target DNA sequence from a ribonucleic acid (RNA) sequence.

18. The method of claim 17, wherein the RNA sequence is a positive control nucleic acid sequence, or the RNA sequence is a nucleic acid sequence from at least one of a mutation, a genotype, a cancer, a infectious agent, a pathogen, a microorganism, a disease, disorder, or condition associated with the RNA sequence, or a combination thereof.

19. A method of diagnosing an infection, disease, disorder, condition, or genotype, the method comprising performing the method of claim 1 to detect a target DNA sequence that is characteristic and/or indicative of the infection, disease, disorder, condition, or genotype.

20. The method of claim 19, wherein the method further comprises amplifying the target DNA sequence in the sample, wherein the sample incubated with the detection mixture is an amplification product, or a portion thereof.

* * * * *